US011478561B2

(12) United States Patent
Gardiner

(10) Patent No.: US 11,478,561 B2
(45) Date of Patent: Oct. 25, 2022

(54) SANITIZATION AND CLEANING SYSTEM FOR OBJECTS

(71) Applicant: Kart Kleen LLC, Snoqualmie, WA (US)

(72) Inventor: Jason Gardiner, Missoula, MT (US)

(73) Assignee: Kart Kleen LLC, Missoula, MT (US)

( * ) Notice: Subject to any disclaimer, the term of this patent is extended or adjusted under 35 U.S.C. 154(b) by 0 days.

(21) Appl. No.: 17/573,617

(22) Filed: Jan. 11, 2022

(65) Prior Publication Data

US 2022/0133926 A1    May 5, 2022

Related U.S. Application Data

(63) Continuation-in-part of application No. 16/368,423, filed on Mar. 28, 2019.

(51) Int. Cl.
*A61L 2/10*    (2006.01)

(52) U.S. Cl.
CPC ............. *A61L 2/10* (2013.01); *A61L 2202/11* (2013.01); *A61L 2202/121* (2013.01);
(Continued)

(58) Field of Classification Search
CPC .. A61L 2/10; A61L 2202/11; A61L 2202/121; A61L 2202/122; A61L 2202/15;
(Continued)

(56) References Cited

U.S. PATENT DOCUMENTS

| 3,179,117 A | 4/1965 | Gibson et al. |
| 3,236,960 A | 2/1966 | Larson |

(Continued)

FOREIGN PATENT DOCUMENTS

| KR | 20130000038 U | * | 1/2013 | ............... A61L 2/10 |
| KR | 20180104955 A | * | 9/2018 | ............... A61L 2/10 |

OTHER PUBLICATIONS

ClorDiSys Solutions, Inc., "Chlorine Dioxide Gas Decontamination: Ultraviolet Light Disinfection," retrieved from <<https://www.clordisys.com/>> on Jan. 15, 2020, available as early as Dec. 26, 2019, 1 page.

(Continued)

*Primary Examiner* — Regina M Yoo
(74) *Attorney, Agent, or Firm* — Lee & Hayes, P.C.

(57) ABSTRACT

An apparatus may include one or more light components that are configured to emit light to sanitize and disinfect one or more objects included within the apparatus. The apparatus may have an interior cavity at which the light components are located, where the interior cavity is accessible via one or more doors, an opening, a lid, etc. The apparatus may have a conveyor that transports objects from a first end of the apparatus to a second end of the apparatus, where the objects are sanitized during transport. The apparatus may be transitioned from an expanded configuration to an unexpanded/collapsed configuration, and vice versa. The apparatus may be stationary or include wheels or other mechanisms that allow the apparatus to be moved between different locations. Objects that are sanitized by the light components of the apparatus will be free of pathogens (e.g., viruses, bacteria, etc.) that are potentially harmful to humans.

20 Claims, 24 Drawing Sheets

(52) U.S. Cl.
CPC ..... *A61L 2202/122* (2013.01); *A61L 2202/15* (2013.01); *A61L 2202/16* (2013.01)

(58) Field of Classification Search
CPC ............. A61L 2202/16; A61L 2202/14; A61L 2209/212; A61L 2209/22; A61L 2/18; A61L 2/22; A61L 9/145; A61L 9/20
See application file for complete search history.

(56) References Cited

U.S. PATENT DOCUMENTS

| | | | |
|---|---|---|---|
| 3,444,867 | A | 5/1969 | Thornton |
| 3,698,029 | A | 10/1972 | Pulliam |
| 4,279,263 | A | 7/1981 | Pulliam |
| 4,992,247 | A | 2/1991 | Foti |
| 5,258,162 | A | 11/1993 | Andersson et al. |
| 5,622,196 | A | 4/1997 | Luongo |
| 5,792,435 | A | 8/1998 | Mueller et al. |
| 5,879,648 | A | 3/1999 | Hada et al. |
| 6,077,480 | A | 6/2000 | Edwards et al. |
| 6,090,218 | A | 7/2000 | Brackmann et al. |
| 6,120,730 | A | 9/2000 | Palaniappan et al. |
| 6,702,985 | B1 | 3/2004 | Taggart et al. |
| 7,300,522 | B2 | 11/2007 | Feistmantl |
| 7,346,956 | B2 | 3/2008 | Andre |
| 7,516,967 | B2 | 4/2009 | Schwei et al. |
| 7,621,285 | B2 | 11/2009 | Robert et al. |
| 8,071,021 | B2 | 12/2011 | Hill |
| 8,349,272 | B2 | 1/2013 | Hill |
| 8,621,824 | B2 | 1/2014 | Mielnik et al. |
| 2002/0159915 | A1 | 10/2002 | Zelina et al. |
| 2003/0037812 | A1* | 2/2003 | Stewart ................. E04H 1/1277 135/96 |
| 2005/0217701 | A1 | 10/2005 | Holbrook |
| 2005/0276722 | A1 | 12/2005 | Hilton |
| 2006/0151714 | A1 | 7/2006 | Thilly et al. |
| 2006/0186358 | A1 | 8/2006 | Couvillion |
| 2007/0012340 | A1 | 1/2007 | Jones et al. |
| 2008/0178412 | A1 | 7/2008 | Kiter |
| 2009/0050174 | A1 | 2/2009 | Gheparde |
| 2010/0122717 | A1 | 5/2010 | Yoon et al. |
| 2011/0068496 | A1 | 3/2011 | Atkinson et al. |
| 2012/0219387 | A1 | 8/2012 | Atkinson et al. |
| 2013/0078327 | A1 | 3/2013 | Adriansens |
| 2017/0156376 | A1 | 6/2017 | Van Appeldoorn et al. |
| 2017/0340760 | A1 | 11/2017 | Starkweather et al. |
| 2020/0237952 | A1* | 7/2020 | Yang ....................... B65B 55/02 |
| 2020/0306395 | A1 | 10/2020 | Gardiner et al. |

OTHER PUBLICATIONS

Dall, "UV-light cleaning shown to cut superbugs hospital-wide," retrieved from <<http://www.cidrap.umn.edu/news-perspective/2018/06/uv-light-cleaning-shown-cut-superbugs-hospital-wide>> on Jan. 22, 2020, CIDRAP News, University of Minnesota, Jun. 5, 2018, 2 pages.

Duke Health, "UV light can aid hospitals' fight to wipe out drug-resistant superbugs," retrieved from <<https://www.sciencedaily.com/releases/2017/01/170117083836.htm>> on Jan. 22, 2020, ScienceDaily, Jan. 17, 2017, 2 pages.

Nikitovic-Jokic, et al., "Portable Ultraviolet Light Surface-Disinfecting Devices for Prevention of Hospital-Acquired Infections: A Health Technology Assessment," Ontario Health Technology Assessment Series, Health Quality Ontario, vol. 18, No. 1, Feb. 2018, pp. 1-73.

Office Action for U.S. Appl. No. 16/368,423, dated Jan. 6, 2021, Gardiner, "Sanitization and Cleaning System for Objects", 17 pages.

Office Action for U.S. Appl. No. 16/368,423, dated Jun. 15, 2021, Gardiner, "Sanitization and Cleaning System for Objects", 24 pages.

Office Action for U.S. Appl. No. 16/368,423, dated Dec. 16, 2021, Gardiner, "Sanitization and Cleaning System for Objects", 22 pages.

PCT Search Report and Written Opinion dated Jun. 15, 2020 for PCT Application No. PCT/US2020/025087, 12 pages.

Proximity Systems, "Ultraviolet Disinfection With UV-CLEAN No Touch Technology," retrieved from <<https://proximitysystems.com/uvclean/>> on Jan. 15, 2020, available as early as Dec. 26, 2019, 6 pages.

Atlantic Ultraviolet, "Sani-Ray Germicidal Ultraviolet Fixtures Owner's Manual: Installation, Operation & Maintenance," Oct. 2018, 12 pgs.

Atlantic Ultraviolet, "Sani-Ray Germicidal Ultraviolet Recessed Fixtures," Specifications, Aug. 2018, 12 pgs.

Surfacide, "Meet the Helios System," retrieved from <<http://www.surfacide.com/>> on Jan. 15, 2020, available as early as Dec. 26, 2019, 9 pages.

The Buggy Bath, "Shopping Cart Cleaning System: The Buggy Bath Shopping Cart Sanitizing," retrieved from <<http://www.thebuggybath.com/>> on Jan. 15, 2020, available as early as Dec. 26, 2019, 1 page.

Comfort Mechanical Enterprises, Inc., "Ultra Clean: Ultra Clean Medical Module," retrieved from <<http://cmeincorporated.com/energy-efficiency-products/ultra-clean-2/>> on Jan. 15, 2020, available as early as Dec. 26, 2019, 5 pages.

American Ultraviolet, "Healthcare Solutions: UVC for Healthcare," retrieved from <<https://www.americanultraviolet.com/germicidal-healthcare-solutions/>> on Jan. 15, 2020, available as early as Dec. 26, 2019, 1 page.

Wiseguide, "4 Best UV Light Sanitizers for Chemical Free Cleaning," retrieved from <<https://www.wiseguide.com/tech/4-best-uv-light-sanitizers-because-you-always-wanted-to-clean-like-harry-potter/>> on Jan. 15, 2020, available as early as Dec. 26, 2019, 5 pages.

* cited by examiner

SANITIZATION AND CLEANING SYSTEM FOR OBJECTS

CROSS-REFERENCE TO RELATED APPLICATIONS

This application is a continuation-in-part application of, and claims priority to, co-pending, commonly-owned U.S. patent application Ser. No. 16/368,423 filed on Mar. 28, 2019, which is incorporated herein in its entirety by reference.

BACKGROUND

On a daily basis, people physically contact, without protection, potentially contaminated objects. Objects may include door handles, tables, rails, benches, shopping carts, and the like. In addition, some retail and non-retail environments may assist in contaminating various objects contained within their respective environments. For instance, medical facilities (e.g., hospitals) and food preparation facilities (e.g., grocery stores or restaurants), as a by-product of their operation, may contribute to the contamination of objects. Further, sensitive environments may need to be sanitized by virtue of their relationship to the public. For instance, medical facilities and food preparation environments need to be regularly cleaned and sanitized to preserve public health and to reduce the number of pathogens and illness causing agents that may be exposed to patents and customers. It is also important for these environments, and their associated institutions and businesses, to satisfy present, and potentially future, legal and regulatory standards relating to public health and safety.

BRIEF DESCRIPTION OF THE DRAWINGS

The detailed description is set forth with reference to the accompanying figures. In the figures, the left-most digit(s) of a reference number identify the figure in which the reference number first appears. The use of the same reference numbers in different figures indicates similar or identical items or features.

DETAILED DESCRIPTION

Figure 1:
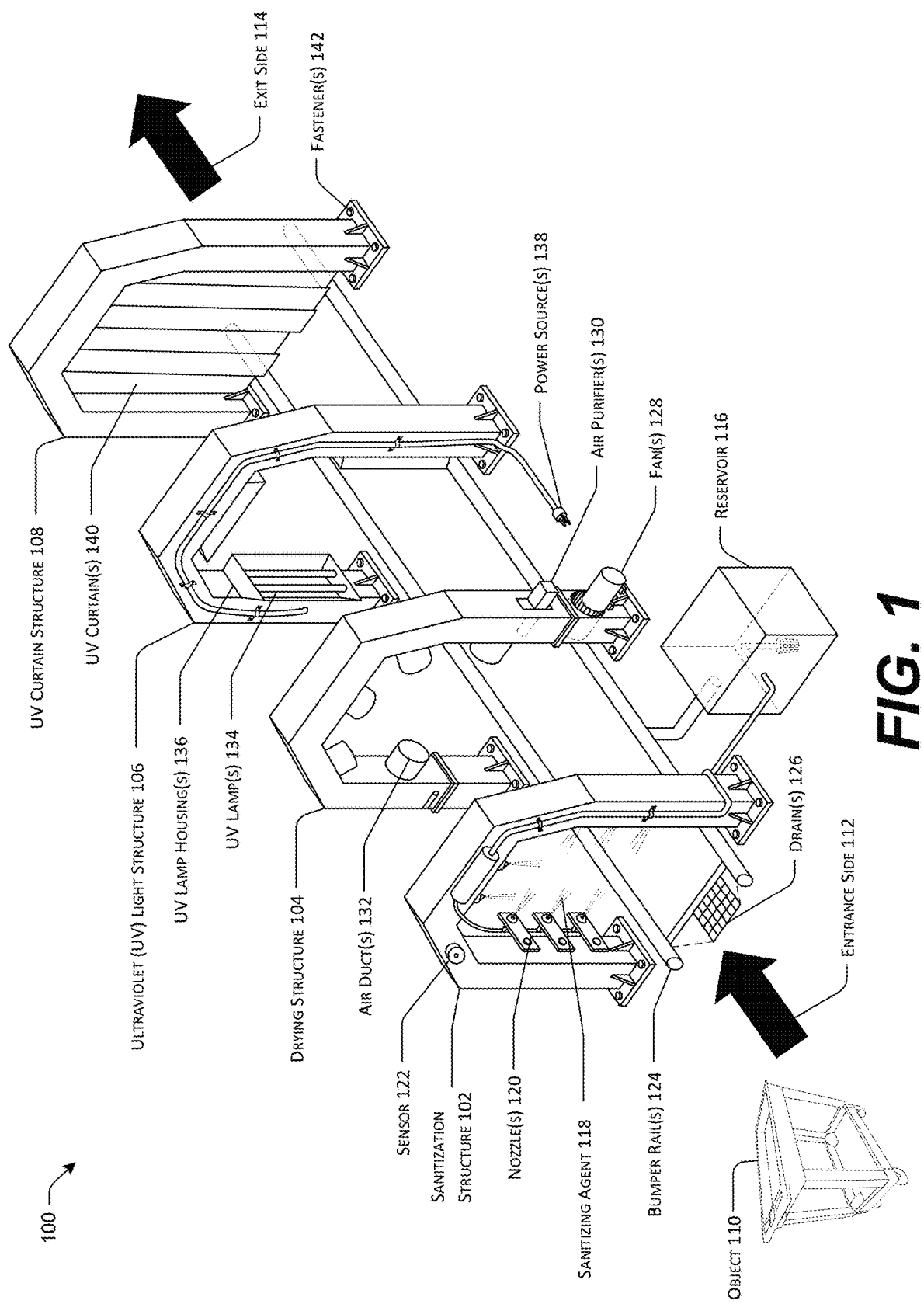
FIG. 1 is a pictorial diagram of an illustrative system that includes multiple structures to facilitate sanitization of one or more objects.

In the context of public health and safety, people in public and private spaces encounter microorganisms on a daily basis. Some of these microorganisms may be harmful to people. A pathogen (i.e., a germ) may be any type of microorganism that may cause or produce a disease or illness. *E. coli* (i.e., a pathogenic bacteria) may cause at least food poisoning that is harmful to humans. In addition, instances of *E. Coli* with respect to food products frequently cause recalls of those food products due to potential food contamination. A recall, such as a request from a store, a manufacturer, or a producer to return a contaminated product, may cause costly disruptions in the business. In particular, a physical environment (e.g., a retail store, a grocery store, or a medical facility) may have a steady flow of people physically interacting with objects (e.g., door handles or shopping carts) during their hours of operation and, therefore, may be susceptible to harboring harmful pathogens. For instance, food preparation businesses including restaurants and delis may be vulnerable to harboring *E. coli* due to the nature of their business handling raw and uncooked food. Therefore, to protect the health of safety of customers, it may be necessary to ensure the sanitization of objects that may be in physical contact with consumers, customers, employees, etc. In addition, limiting the exposure of potentially harmful pathogens may benefit businesses by avoiding the consequences of harboring potentially harmful pathogens (e.g., avoiding recalls).

With respect to the sanitization of physical objects, there is a need for techniques, including processes and apparatuses, that facilitate efficient, high-quality, and reliable sanitization of physical objects. In particular, physical objects, which may be interchangeably referred to as "objects" or "items" herein, may be located within a physical environment (e.g., a grocery store). These objects (e.g., shopping carts, hospital beds, wheelchairs, etc.) may be accessible for physical contact by customers and/or employees. Because these objects are physically handled by customers and/or employees during the course of business, and since these objects may be in physical contact with food items (e.g., raw chicken, unclean produce, etc.), human waste (e.g., feces, urine, vomit, etc.) or other bodily fluids (e.g., saliva, blood, etc.), etc., there is a need to sanitize the objects regularly to guard against potentially harmful pathogens that attach to the objects. For instance, a shopping cart may be physically interacted with by multiple customers during the course of a single day. If the shopping cart were to be harboring a harmful pathogen, each of the multiple customers that handled the shopping may be unwittingly exposed to the harmful pathogen.

Traditional techniques to clean shopping carts for use in a grocery store may include pressure washing or using a towel or scrub brush to wipe down the shopping cart. However, these techniques often neglect eliminating sanitation threats at a microbial level. Further, these techniques may result in wear and tear of an object because they require either physically dislodging contaminants under high pressure (e.g., a pressure of 750 to 30,000 pounds per square inch (PSI)) or physically touching the object.

In addition, there is a need for efficient, high-quality, and reliable results sanitizing multiple objects at a single time or consecutively. In a physical environment, (e.g., a grocery store), there may be additional challenges with implementing sanitization techniques for objects (e.g., shopping carts). For instance, a grocery store may have a designated area for cleaning various equipment. This designated area may be a confined and/or limited in area (e.g., limited as to a quantity of square feet). Therefore, there is a need to develop at least a system, and associated processes, that can operate in an area having a limited amount of space. In light of area related limitations, traditional techniques have included placing a shopping cart in a container, closing a door or bringing down a lid over the container, and starting a cleaning cycle similar to a dish washing machine type technique. However, these techniques may be time-consuming and do not allow for multiple objects (e.g., stacked shopping carts) to be run through the cleaning process efficiently. In addition, these traditional techniques do not allow for multiple and/or different sanitization techniques to be applied to a single object. As described herein, the systems and processes described herein describe the application of a sanitizing agent (e.g., a chemical solution) and ultraviolet (UV) light to an object. Existing systems are unable to accommodate multiple disinfecting techniques. Other existing techniques may include wiping the object off using a cleaning tool (e.g., a towel or a scrubbing brush) or pressure washing the object. However, these techniques may be time consuming and may be inefficient for cleaning multiple objects, either at a single time or consecutively. Further, these techniques may not reliably produce a consistent sanitization quality as the cleanliness of the cleaning object and/or the manual effort used to sanitize the object may vary. In addition, traditional techniques may result in wear and tear on the object as they require physical interaction with the object.

The systems and techniques described herein address the above challenges with respect to cleaning and sanitizing objects. For instance, the systems and techniques herein describe an efficient and repeatable apparatus and process to sanitize an object (or multiple objects). In addition, the systems and techniques herein describe a system that may be used to sanitize multiple objects efficiently and in a timely manner. Further, the systems and techniques herein also include sanitizing objects via an automated or a partially-automated process. These systems and techniques describe a primarily touchless process to sanitize an object in order to reduce wear and tear and/or damage to the object that could potentially occur as a result of the sanitization process. The techniques as described herein are suitable for a number of physical environments including at least grocery stores (or other physical stores where shopping carts are used), locations where raw or uncooked food products are handled, processed, and/or prepared (e.g., restaurants, food processing locations, etc.), and medical facilities (e.g., hospitals, medical clinics, etc.).

The techniques described herein are directed to a sanitization system. In some embodiments, the sanitization system may include a sanitization structure, a drying structure, an ultraviolet (UV) light structure, and/or a UV curtain structure. The various structures may be axially aligned such that an object (e.g., a shopping cart, a hospital bed, a table used to process/prepare food products, etc.) may be received by a first structure (e.g., the sanitization structure or the UV light structure) at an entrance side (i.e., a first side). For instance, the first structure may be an arch or an arch frame (or any other shape, such as rectangular, circular, etc.) with a space with a width (e.g., a span) underneath a horizontal beam or curved arch. The first structure may receive the shopping cart in this space. The shopping cart may then exit the sanitization system at an exit side (i.e., a second side) of a second structure (e.g., the drying structure, the UV light structure, or the UV curtain structure). The sanitization structure, the drying structure, the UV light structure, and/or the UV curtain structure may be permanently or removably fastened/coupled to the ground and/or a surface (e.g., a platform and/or a ramp). However, the structures described herein may also be mobile in nature, and may be moved in any direction using wheels, rollers, a slider, etc. In some instances, an "entrance" or "enter" sign may be coupled on an entrance side of one or more of the sanitization structure, the drying structure, the UV light structure, or the UV curtain structure. In addition, an "exit" sign may be coupled to an exit side of one or more of the sanitization structure, the drying structure, the UV light structure, or the UV curtain structure. That way, an individual that is facilitating the sanitization of the object(s) may determine an entrance point of the sanitization system.

In various embodiments, the shopping cart may move or may be moved a distance spanning from the entrance side (e.g., an entrance side of the sanitization structure) to the exit side (e.g., the exit side of the UV curtain structure) via manual and automated means. With respect to manual means, one or more objects (e.g., shopping carts) may be pushed or pulled by hand to move the distance spanning from the entrance side to the exit side. One or more objects may also be pulled or pushed using a rope (e.g., a control rope coupled to the object), a chain link, a lead, a braided hose, or other suitable flexible and/or rigid devices. In various embodiments, the object may be received at the entrance side and travel the distance to the exit side using automated means. For instance, the shopping cart may be placed on a conveyer belt, a moving sidewalk (e.g., an auto walk), an escalator (e.g., an inclined moving sidewalk), a shuttle that is coupled to a track and/or grooves, an object conveyer that couples to the object, or other suitable automated devices that move the object(s) from a first side of the sanitization system (e.g., the entrance) to a second side of the sanitization system (e.g., the exit).

In various embodiments, the sanitization structure may be coupled to a reservoir that contains a sanitizing agent. The sanitization structure may include a sanitizing agent tube that connects one or more nozzles to the reservoir, such that the sanitizing agent is in fluid communication contained in the reservoir is in fluid communication with the nozzle(s). The reservoir cause filtered water to be mixed with the sanitizing agent such that the filtered water/sanitizing agent combination is dispersed by the one or more nozzles. The one or more nozzles may be configured to apply the sanitizing agent to the shopping cart. For instance, the nozzles may mist the shopping cart with a layer of the sanitizing agent. The sanitizing agent may be any anti-microbial sanitation solution or any anti-bacterial chemical that can disable, remove, or destroy potentially harmful pathogens. In some instances, the one or more nozzles may apply the sanitizing agent in continuous manner or at an interval. The sanitizing agent may be configured to be evaporable.

In various embodiments, the drying structure may include one or more fans, or one or more directional blowers, that are configured to draw in air from the atmosphere and/or a gas. An air purifier 130 may then receive the air, filter out particulates (e.g., dust), to produce filtered air. The drying structure may also include one or more air ducts to apply the filtered air to the shopping cart. The one or more fans, the air purifier 130, and the one or more air ducts may be coupled and/or connected via purification tunnel. The purification tunnel may be a tube and/or pipe that facilitates the movement of a gas (e.g., the filtered air). The filtered air may be applied via the one or more air ducts to remove moisture present on the shopping cart. For instance, the filtered air may dry the sanitizing agent such that little to no sanitizing agent remains on the object(s). In other embodiments, an object may be previously wet (e.g., a shopping cart being wet as a result of rainy or snowy weather). The drying structure may apply the filtered air to the object to dry the object. In some instances, as stated above, the one or more nozzles may apply the sanitizing agent in continuous manner or at an interval. However, in some instances, an object may not have the sanitizing agent applied via the sanitization structure, or the sanitization structure may not be present in the sanitization system, and the object may be moved towards the drying structure to be dried. In some instances, the air purifier 130 may be an air scrubber that removes gases or particles from the air. For instance, an air scrubber may be used to remove carbon dioxide from the air.

In various embodiments, the UV light structure may include one or more UV lamps that are configured to apply UV light to the shopping cart. The one or more UV lamps may be configured to emit light at a wavelength outside of the visible spectrum that disables, breaks down, and/or destroys pathogenic organisms (e.g., bacteria). The one or more lamps may be housed in one or more UV lamp housings 136 to provide directional application of the UV light to the shopping cart.

In various embodiments, the UV curtain structure may include one or more UV curtains. The one or more UV curtains may be configured to block an entirety or a portion of the UV light emitted from the one or more UV lamps. In some instances, the sanitization structure, the drying structure, the UV light structure, and/or the UV curtain structure may be encapsulated or surrounded by a tunnel. The tunnel may be co-axially aligned with at least one of the sanitization structure, the drying structure, the UV light structure, or the UV curtain structure. The tunnel may have an entrance side and an exit side. In some instances, the tunnel may be made from a polyethylene material that reduces visibility of processes performed by the sanitization structure, the drying structure, the UV light structure, and/or the UV curtain structure. That is, customers may only see the tunnel, and may not have visibility of the techniques used by the structures to clean and sanitize objects.

In various embodiments, bumper rails may extend from the sanitization structure (or any other of the structures) to at least one of the drying structure, the UV light structure, or UV curtain structure. For instance, the sanitization structure may be an arch with an inner side located adjacent to the space within or beneath the arch. The UV curtain structure may have a similar arch structure. A first bumper rail may extend from a first side, of the inner side of the sanitization structure, to a first side, of the inner side of the UV curtain structure. A second bumper rail may extend from a second side, of the inner side of the sanitization structure, to a second side, of the inner side of the UV curtain structure. The second bumper rail may be parallel or near-parallel to the first bumper rail. The bumper rail may be configured to cause the object to only be able to exit the sanitization system at an exit side of the sanitization system. A drain (e.g., a grated floor) may span at least a portion of the width between the first bumper rail and the second bumper rail. The drain may collect any fluid (e.g., sanitizing agent) that is applied to the object(s) and that drips from the object(s), or any fluid that is not applied directly to the object(s) and collects on a surface underneath or around the object(s). In some instances, the drain may include a funnel underneath the grated floor for collection of unused sanitizing agent (or sanitizing agent that is applied to the object(s) and that drips/falls off).

In various embodiments, a sensor (e.g., a motion sensor) may be located on or coupled to at least one of the sanitization structure, the drying structure, the UV light structure, and/or the UV curtain structure. The sensor may be configured to detect the object when the object is within a threshold distance (e.g., 1 foot, 2 feet, 5 feet, 10 feet, etc.) from one of the structures. In response to detecting the object, at least one of the sanitization structure, the drying structure, the UV light structure, and/or the UV curtain structure may activate (e.g., commence application of the sanitizing agent, gas current, and/or UV light). For instance, in response to detecting the object(s) (e.g., a single shopping cart, multiple stacked shopping carts, etc.), the sanitization structure may activate to apply the sanitizing agent to the object. The sanitization structure, the drying structure, the UV light structure, and/or the UV curtain structure may also de-activate or cease operation if the motion sensor no longer detects the object(s). For instance, provided that the sensor is positioned on the sanitization structure directed towards the entrance of the sanitization system, the sensor may detect the object(s) when they come in proximity to the sanitization structure. Upon detection, the nozzle(s) of the sanitization structure may apply or disperse the sanitizing agent. Once the object(s) move underneath or through the sanitization structure, the sensor may no longer detect the object(s). As a result, the nozzle(s) may cease applying/dispersing the sanitizing agent, since there are no objects that are currently underneath the sanitization structure.

In various embodiments, a timer and a display may be coupled to at least one the sanitization structure, the drying structure, the UV light structure, the UV curtain structure, and/or an interior or exterior of the tunnel. In response to detecting the object(s), a timer may count down or count up to a predetermined sanitization time. For instance, when the object(s) are detected, a time counting down from six seconds (i.e., the predetermined sanitization time) may begin. In some instances, upon the predetermined sanitization time being reached (e.g., the object(s) have been within the sanitization system for at least six seconds), an audible cue may be emitted from a speaker and/or another audio device to indicate the predetermined sanitization time has been reached. Alternatively, a visual cue may be displayed via the display that indicates that the predetermined sanitization time has been reached. The predetermined sanitization time may be a time that represents a standardized amount of time that an object should spend in the sanitization system in order to meet a threshold sanitization level. The threshold sanitization level may be a predetermined sanitization level associated with removing at least a majority of (or a different level, such as 90%, 95%, 99%, etc.) potentially harmful pathogens. In some instances, a timer may be coupled to the sanitization structure, the drying structure, the UV light structure, the UV curtain structure, and/or the tunnel. An operator of the sanitization system may utilize the timer to determine a length of time the object(s) spend in the sanitization system.

In various embodiments, a power source (e.g., a source of electric power) may be a component that supplies power to at least one of the sanitization structure, the drying structure, the UV light structure, and/or the UV curtain structure. In some instances, a separate power source may supply electric power to each structure, a single power source may supply electric power to each of the structures, or different power sources may supply electric power to multiple, but not all of, the structure.

In various embodiments, one or more of the sanitization structure, the drying structure, the UV light structure, or the UV curtain structure may be coupled to an emergency shut-off. An emergency shut-off may be a manual button or switch (or a selectable element actuable via the display) that turns-off, de-activates, and/or shuts down one or more of the sanitization structures, such as the sanitization structure, the drying structure, and/or the UV light structure. For instance, the emergency shut-off may be a lever that, when manually switched by an operator of the sanitization system, immediately ceases application of the sanitizing agent by the sanitization structure.

In various embodiments, the sanitizing agent may be applied to the object via one or more nozzles coupled to the sanitizing structure at a first time, the gas current may be applied to the object via one or more air ducts coupled to the drying structure at a second time that is subsequent to the first time, and UV light may be applied via one or more UV lamps coupled to a UV light structure at a third time that is subsequent to the second time. However, the different structures of the sanitization system described herein may be arranged in any order or configuration. For instance, the sanitization structure may apply the sanitizing agent first, the UV light structure may apply the UV light second, and then the drying structure may apply the purified air last. In further embodiments, provided that the structures are moveable, the structures may be moved between different configurations or arrangements.

In certain embodiments, the object may pass through a tunnel or tube made of a rigid or semi-rigid material, such as plastic, any type of metal, etc. Instead of the object being moved through the tunnel/tube via a conveyor system, the object may be moved through the tunnel/tube via one or more wheels coupled to an interior surface of the tunnel/tube. For instance, as the object is placed into the tunnel/tube, wheels on the interior side of the tunnel/tube may make contact with the object, and the wheels may cause the object to move through the tunnel/tube while the object is being sanitized or disinfected.

An illustrative system may include a disinfection locker, which may include one or more doors and an interior cavity that includes a reflective surface on at least one of the interior walls within the interior cavity, one or more lighting components (e.g., UV lamps, Ultraviolet C (UVC) lamps, etc.), and a mechanism that is used to hang an object that is to be sanitized and/or disinfected by the UV/UVC light illuminated from the lamps. In particular, the locker may include two doors, where at least one of the doors includes a control panel that is used to operate the lamps. The lamps may be situated in different locations within the interior cavity of the locker and, when an object to be sanitized is placed within the locker, the lamps may be activated via the control panel to sanitize/disinfect the object. In some embodiments, the object may be clothing, hospital gowns, medical clothing, towels, etc. that are hung from a bar or other structure within the interior cavity of the locker.

Another illustrative system may include a housing, an entrance side, an exit side, and a conveyor within an interior of the housing that transports an object from the entrance side to the exit side. The interior of the system includes one or more lighting components (e.g., UV lamps, UVC, lamps, etc.) that emit light (e.g., UV light, UVC light, etc.) that sanitize and disinfect the object. For instance, for an object that is to be sanitized, the object is placed on the conveyor on the entrance side of the system, the conveyor transports the object through the system where the light emitted by the lighting component(s) sanitizes the object. The object is then removed from the system via the exit side of the system. The system may be stationary or mobile and, in the mobile embodiment, the system may have wheels or a different mechanism that are used to move the system. The system may also include some type of mechanism (e.g., a UV curtain) that prevents the light from exiting the system.

An illustrative system may include a container, bag, box, etc. that includes a structure that includes one or more lighting components that emit light (e.g., UV light, UVC light, etc.). The system, including the structure contained therein, may be converted between an expanded state when in use to an unexpanded or collapsed state when not currently in use. The system may include a top surface and a lid that opens and closes such that an object can be placed within the system. Upon closing the lid, the light emitted by the lighting component(s) sanitizes and disinfects the object and, once sanitized, the object may be removed from the system via the lid. The lid may remain closed using one or more fasteners, such as buckles, a zipper, clasps, Velcro®, etc. Since the size of the system may vary based on transitioning the system from the expanded state to the unexpanded/collapsed state, the system may be easily transportable.

In some embodiments, a system may include a housing, one or more doors, and an interior cavity within the housing that includes one or more lighting components that emit light (e.g., UV light, UVC, light, etc.). An object may be placed within the interior cavity and may be sanitized by the light emitted from the lamp(s). Examples of object that may be placed within the system may include personal protective equipment (PPE), such as facial masks, goggles, glasses, gowns, headwear, etc. The lamps may be activated/deactivated via one of more control components located on an exterior surface of the housing. Moreover, the system may be stationary or mobile using wheels. In a mobile state, the system may be moved between different locations/areas to sanitize/disinfect different objects.

FIG. 1 is a pictorial diagram of an illustrative apparatus that includes multiple structures to facilitate sanitization of one or more objects. The pictorial diagram 100 includes at least a sanitization structure 102, a drying structure 104, a UV light structure 106, and a UV curtain structure 108. The sanitization structure 102, the drying structure 104, the UV light structure 106, and/or the UV curtain structure 108 may be axially aligned. In some instances, at least one of the sanitization structure 102, the drying structure 104, the UV light structure 106, and/or the UV curtain structure 108 may not be axially aligned with the various other structures. As shown, each of the sanitization structure 102, the drying structure 104, the UV light structure 106, and/or the UV curtain structure 108 may be configured to receive an object 110 at an entrance side 112. As shown, the object 110 may be received by the sanitization structure 102 at the entrance side 112 and exit the UV curtain structure 108 at an exit side 114. In some instances, each of the sanitization structure 102, the drying structure 104, the UV light structure 106, and/or the UV curtain structure 108 may individually have an exit and an entrance. For instance, the sanitization structure may have an entrance on the entrance side 112 (e.g., where the object 110 enters the sanitization structure 102) and an exit on the opposite side or exit side 114 (e.g., where the object 110 exits the sanitization structure 102).

The object 110 may be any unpowered or a powered object 110. An unpowered object 110 may include objects 110 that require external assistance to move, unless the unpowered object(s) 110 are moved via an automated or partially-automated mechanism, such as a conveyor. For instance, an unpowered object 110 may include a shopping cart, a push cart, a pallet, a table (e.g., for handling, processing, or preparing facility, such as a hospital bed). In some instances, the object 110 may be a plurality of objects 110. For instance, the object 110 may be a plurality of stacked shopping carts where a shopping cart of the plurality of shopping carts is configured to physically couple to another shopping cart of the plurality of shopping carts. If the object 110 requires external assistance to move, the object 110 may be moved using a suitable manual device (e.g., a rope operated by a person) or automated device (e.g., a conveyor) to travel a distance between the entrance side 112 and the exit side 114. An object 110 may also be a powered object 110 that is able to travel the distance between the entrance side 112 and the exit side 114 with assistance. For instance, the powered object 110 may include a self-driving cart or a motor vehicle that includes at least a motor or battery and a means for navigation (e.g., sensors). As shown, the object 110 illustrated in FIG. 1 appears to depict a push cart that may require external assistance to travel the distance between an entrance side 112 and an exit side 114 of the sanitization system.

In some embodiments, the object(s) 110 may be of any size and the sanitization system 100 may also be of any size. That is, the sanitization system 100 may be of any height, length, and/or width. For instance, the sanitization system 100, as well as the various structures associated therewith (e.g., the sanitizing structure 102, the drying structure 104, the UV light structure 106, and/or the UV curtain structure 108), may be of suitable size in order to allow the object(s) 110 to pass through, by, or underneath the structures. For instance, and as described herein, the sanitization system 100 may clean/sanitize smaller objects 110, such as shopping carts, hospital beds, wheelchairs, food preparation carts/tables, etc. However, the sanitization system 100 may be of a suitable size to clean/sanitize larger objects 110, such as trucks that transport livestock (e.g., livestock trailers that transport cows, horses, etc.) or food products (e.g., grain, hay, produce, etc.), food conveyor belt trucks, grain truck beds, food trailers, farming equipment (e.g., tractors, plows, irrigation equipment, etc.), and so on. For the purposes of this discussion, the sanitization system 100 may be built to any size and/or may be adjustable to any size, thereby allowing the sanitization system 100 to clean and sanitize objects 100 of any size.

As shown, the sanitization structure 102 may be coupled to a reservoir 116. The reservoir 116 may include a container that is configured to hold liquid such as water and/or a cleansing agent. In some instances, the reservoir 116 may include a filter that is configured to filter water or the cleansing agent (e.g., remove particles and/or contaminants from water/cleansing agent). The cleansing agent may be composed of anti-pathogen compounds such as triclosan, triclocarban, benzalkonium chloride, benzethonium chloride, chloroxylenol, and/or other suitable compounds that at least assist in destroying, disabling, and/or removing pathogens. The cleansing agent may be a chemical that destroys, removes, and/or disables pathogens, bacteria, food items, dirt, etc. In some instances, a liquid and a cleansing agent may be combined to form a sanitizing agent 118. Alternatively, the cleansing agent itself may be the sanitizing agent 118. The sanitizing agent 118 may be a liquid sanitizer that is configured as an anti-microbial sanitization solution. As shown, the reservoir 116 is coupled to one or more nozzles 120 via one or more tubes or pipes that transport the sanitizing agent 118 from the reservoir 116 to the nozzle(s) 120. The one or more nozzles 120 may be configured to apply or disperse a mist or spray of the sanitizing agent 118 onto the object(s) 110. In some instances, the one or more nozzles 120 may include rotating, or movable, misting heads to ensure full coverage of the object(s) 110 with the sanitizing agent 118. The one or more nozzles 120 may also apply a liquid (e.g. water) to the object(s) 110. In some instances, the sanitizing agent 118 may be selected based on a type of pathogen, a group of pathogens, food products, bodily fluids, bacteria, dirt, etc. that may be present on the object(s) 110.

As shown, the sanitization structure 102 may include one or more sensors 122. The sensor(s) 122 may include an active or passive infrared sensor, a microwave sensor, an area reflective sensor, an ultrasonic sensor, a photo optic motion sensor. A, or any other types of sensors that are configured to detect the object(s) 110. The sensor(s) 122 may be any sensor that is configured to detect the object(s) 110. In some instances, the object(s) 110 may be configured to contain a radio transmitter that may send a coded and/or encoded signal (e.g., radio wave) that is received by a receiver on the sensor(s) 122. The sensor(s) 122 may detect the object(s) 110 based on receiving a signal emitted from the object(s) 110. In response to the sensor(s) 122 detecting the object(s) 110, the sanitization structure 102 may activate causing the one or more nozzles 120 to apply the sanitizing agent 118 to the object(s) 110.

As shown, a set of bumper rails 124 may extend from the sanitization structure 102 to the UV curtain structure 108. In some instances, the bumper rail(s) 124 may extend to the drying structure 104 or the UV light structure 106. As shown, a first bumper rail 124 appears to be located on an inside side (e.g., a first side) of the sanitization structure 102 and extends to an inside side (e.g., a first side of UV curtain structure 108). As shown, a second bumper rail 124 appears to be located on an inside side opposite the first side (e.g., a second side) of the sanitization structure 102 and extends to an inside side opposite the first side (e.g., a second side of UV curtain structure 108). As shown, the first bumper rail 124 and the second bumper rail 124 appear to be parallel or near-parallel. In other instances, the first the first bumper rail 124 and the second bumper 124 may not be parallel or near-parallel. For instance, the bumper rail(s) 124 may be a curved or wave shape. The bumper rail(s) 124 may be configured to serve as a guide for the object(s) 110 to follow through the sanitization system. The bumper rail(s) 124 may be composed of at least one of wood, metal, plastic, or other suitable rigid materials.

As shown, one or more drains 126 may span at least a portion of the width between the first bumper rail 124 and the second bumper rail 124. The drain(s) 126 may include a grated floor that spans a distance between the sanitization structure 102 and at least one of the drying structure 104, the UV light structure 106, or the UV curtain structure 108, although the drain(s) 126 may be positioned at any location within the sanitization system 100. In some instances, the drain(s) 126 may be located before a first arch (e.g., the sanitization structure 102 and at least one of the drying structure 104, the UV light structure 106, or the UV curtain structure 108) on the entrance side 112 and/or located after a second arch (e.g., the sanitization structure 102 and at least one of the drying structure 104, the UV light structure 106, or the UV curtain structure 108) on the exit side 114. In some instances, the drain(s) 126 may be located between any grouping of structures, the grouping of structures comprising at least two of the sanitization structure 102 and at least one of the drying structure 104, the UV light structure 106, and the UV curtain structure 108. The drain(s) 126 may be configured to capture liquid and/or the sanitizing agent 118 that has not been applied to the object 110 or has been applied, but run-off, the object 110. In some instances, the drain(s) 126 may include a funnel underneath a grated floor to capture at least unused or run-off of the sanitizing agent 118 that was applied to the object 110.

As shown, the drying structure 104 may include one or more fans 128, one or more air purifiers 130, and one or more air ducts 132. The one or more fans 128 may receive air from the atmosphere (e.g., the area within or surrounding the sanitization system 100). In some instances, the one or more fans 128 may be directional blowers. The one or more fans 128 may be configured move a gas (e.g., air) with an increase in pressure. For instance, a gas may have a first pressure before being drawn in by the one or more fans 128. The one or more fans 128 may cause a movement of the gas at a second pressure, wherein the second pressure is greater than the first pressure. The one or more fans 128 may be coupled to the one or more air purifiers 130. The one or more air purifiers 130, which may be one or more air scrubbers, may receive a gas from the one or more fans 128. The one or more air purifiers 130 may be configured at least to filter the gas to remove contaminants (e.g., dust). In some instances, the one or more air purifiers 130, may transform the gas into a purified gas. For instance, an unfiltered gas may be filtered to remove or to disable pathogens thereby creating a purified (e.g., filtered) gas. The one or more air ducts 132 may receive the purified gas (e.g., a gas current) and apply the gas current to the object(s) 110. At least one air duct 132 of the one or more air ducts 132 may have an air duct opening that is adjustable. For instance, the air duct opening for an air duct 132 may be reduced in size (e.g., reduced in diameter) to apply the gas current to the object 110 at a greater velocity/rate. The one or more air ducts 132 may apply a gas current to dry the object(s) 110 (e.g., to dry any sanitizing agent 118 remaining on the object(s) 110). In some instances, the one or more fans 128, the one or more air purifiers 130, and one or more air ducts 132 may be coupled via a pipe, tunnel, and/or tube that facilitates the movement of gas.

As shown, the UV light structure 106 may include one or more UV lamps 134, one or more UV lamp housings 136, and a power source 138. The one or more UV lamps 134 may apply UV light to the object(s) 110. The one or more UV lamps 134 may be one or more germicidal UV lamps that are configured to emit a light at a wavelength outside of the visible light spectrum to deactivate the deoxyribonucleic acid (DNA) of various pathogens (e.g., bacteria). As shown, the one or more UV lamps 134 may be at least partially contained within the one or more UV lamp housings 136. The one or more UV lamp housings 136 may provide a direction for the one or more UV lamps 134 to emit UV light, thereby assisting in the application of UV light to the object(s) 110. The one or more UV lamp housings 136 may also prevent at least a portion of the UV light emitted from the one or more UV lamps 134 from being emitted in a direction away from the object(s) 110.

As shown, a power source 138 may be coupled to the one or more UV lamps 134 and/or the UV light structure 106 to provide electrical power. As described herein, the power source 138 may be a single power source 138 or multiple power sources 138, and the power source(s) 138 may supply electric power to a single structure, some but not all of the structures, or all of the structures of the sanitization system 100. The power source 138 may have an electrical power setting. For instance, the power source 138 may be at least one of 240 volt (240 v) single phase, 240 v two phase, 240 v three phase, 110-volt single phase, or other suitable voltage and phase settings. In other instances, a second power source 138 may be coupled to the sanitization structure 102 and a third power source 138 may be coupled to the drying structure 104. In some instances, the power source 138 may be coupled to the sanitization structure 102, the drying structure 104, and the UV light structure 106. By way of example, a first power source 138 with a first voltage and/or phase setting may be coupled to at least one of the sanitization structure 102, drying structure 104, or the UV light structure 106, and a second power source 138 with a second voltage and/or phase setting may be coupled at least one of the sanitization structure 102, drying structure 104, or the UV light structure 106. The first voltage and/or phase setting may be different than the second voltage and/or phase setting. The power source 138 may be configured to receive electric power from an electrical producing device or system including receive electrical power via chemical energy, mechanical energy, solar energy, wind energy, geothermal energy, hydrogen energy, hydroelectric energy, and/or biomass energy.

As shown, the UV curtain structure 108 may include, or be coupled to, one or more UV curtains 140. The one or more UV curtains 140 may be a material, such as amber-tinted poly vinyl chloride or other suitable materials, to block at least a portion of the UV light emitted from the one or more UV lamps 134. In some instances, the one or more UV curtains 140 may be configured such that the object 110 may pass through. As shown the UV curtain structure 108 may be fastened or secured to the ground (e.g., concrete) or a surface (e.g., a ramp or platform) via one or more fasteners 142. The one or more fasteners 142 may be based on a material of the ground or surface (e.g., concrete or wood). The one or more fasteners 142 may include screws, anchors, nails, spikes, concrete/cement, adhesive, or other suitable fasteners to permanently or removably fix the UV curtain structure 108 to the ground or to a surface. In addition, the sanitization structure 102, drying structure 104, and the UV light structure 106 may be fixed to the ground or to a surface via one or more fasteners 142 similar to the fasteners 142 coupled to the UV curtain structure 108.

By way of example, a plurality of shopping carts (e.g., the object 110) may be coupled together forming a stack of shopping carts. The plurality of shopping carts may be placed on a moving sidewalk (i.e., automated transported) or pulled via a rope lead (i.e., manually transported) through a sanitization system. The plurality of carts may travel along a path defined by a first and second bumper rail (e.g., one or more bumper rails 124). The plurality of shopping carts may enter a sanitization arch (e.g., the sanitization structure 102) at a first side (e.g., an entrance side 112) of the sanitization arch. A photo optic sensor (e.g., a sensor 122) may detect the plurality of shopping carts. In response to detecting the plurality of shopping carts, the sanitization arch may activate. For instance, a pressurized system may be configured to open a valve allowing the liquid sanitizer (e.g., a sanitizing agent 118 and filtered water) to travel from a reservoir 116 to a plurality of nozzles 120 coupled to the sanitization arch. The liquid sanitizer may be misted or otherwise dispensed via the plurality of nozzles 120 to form a sanitizing layer on the plurality of shopping carts. A drain 126 may be configured to collect run-off of the liquid sanitizer.

The plurality of shopping carts may then travel via automated or manual means to a drying arch (e.g., the drying structure 104). A plurality of fans (e.g., one or more fans 128) may draw air from the atmosphere and increase the pressure of the air on a dispensing side of the plurality of fans 128. The drawn air may pass through an air scrubber (e.g., one or more air purifiers 130) to convert unpurified air to purified air by removing contaminants such as dirt and bacteria. The purified air may be applied to the plurality of shopping carts as they pass underneath the arch to dry off any excess liquid sanitizer. The plurality of shopping carts may then travel to a UV light arch (e.g., a UV light structure 106). Germicidal UV light may be applied to the plurality of shopping carts that may disable or destroy one or more pathogens. A UV curtain arch (e.g., the UV curtain structure 108) may block at least a portion of the UV light to protect passersby. The plurality of shopping carts may exit the UV curtain arch at an exit side of the UV curtain arch (e.g., the exit side 114). The photo optic sensor 122 may detect that there are no remaining shopping carts present in the sanitization system and cause the sanitization arch, the drying arch, and the UV light arch to cease operation and/or to shut down. The entire sanitization system may be encapsulated or encompassed by a tunnel 202 that is composed of a rigid material that can block or resist at least the liquid sanitizer, the purified air, and the UV light. As a result of applying a sanitizing agent 118, purified air, and/or UV light to the shopping carts, which will disable, destroy, and/or remove substances (e.g., bacteria, pathogens, body fluids, human waste, dirt, food products, etc.) residing on the shopping carts, the shopping cars will be cleaned and sanitized for subsequent use. The sanitization system described herein will reduce, and possibly eliminate, the likelihood that individuals (e.g., employees, customers, etc.) will be exposed to potentially harmful substances.

Figure 2:
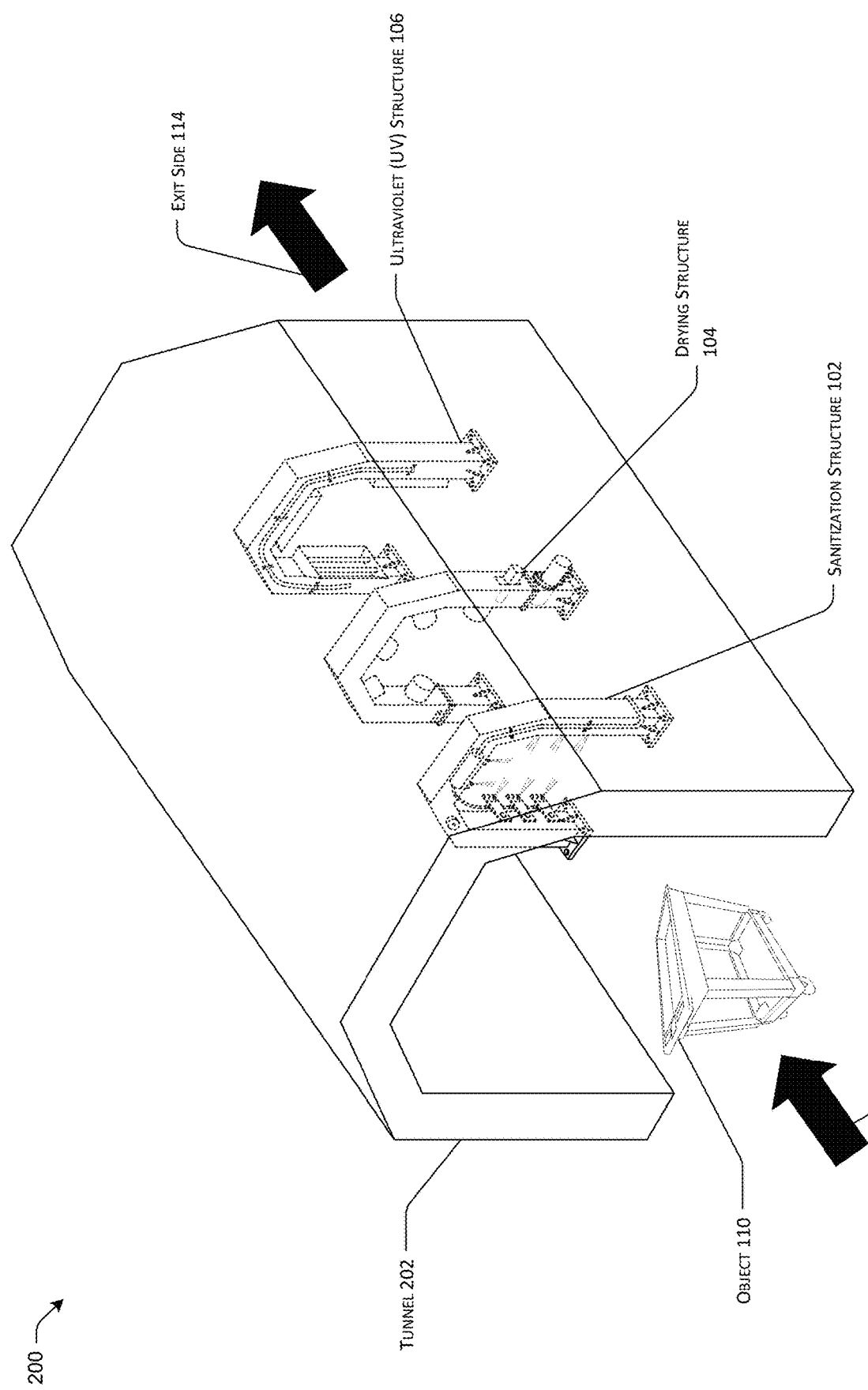
FIG. 2 is a pictorial diagram of an illustrative system that includes a tunnel that at least partially encloses multiple structures that facilitate sanitization of one or more objects.

FIG. 2 is a pictorial diagram 200 of an illustrative apparatus that includes a tunnel 202 that at least partially encloses multiple structures. As shown, the tunnel 202 appears to encapsulate or enclose at least the sanitization structure 102, the drying structure 104, and the UV light structure 106. The tunnel 202 may also encapsulated or enclose the UV curtain structure 108. As shown, the object(s) 110 appear to be depicted entering the tunnel on the entrance side 112. The tunnel 202 may be configured to have a tunnel entrance on a first side (e.g., the entrance side 112), and tunnel exit on a second side (e.g., the exit side 114). In some instances, the tunnel 202 may be composed of a high-density polyethylene. In other instances, the tunnel 202 may be composed of plastic, wood, metal, or similar rigid materials. The tunnel 202 may be composed of a material that blocks or is resistant to the sanitizing agent 118 and/or UV light. In various embodiments, the sensor 122 may be coupled to the tunnel 202 for detecting the object 110. The tunnel 202 may be coupled to some, all, or none of the structures of the sanitization system 100. For instance, some or all of the structures may provide support for the tunnel 202, or the tunnel 202 may be freestanding and may not require support from any of the structures of the sanitization system 100.

Figure 3:
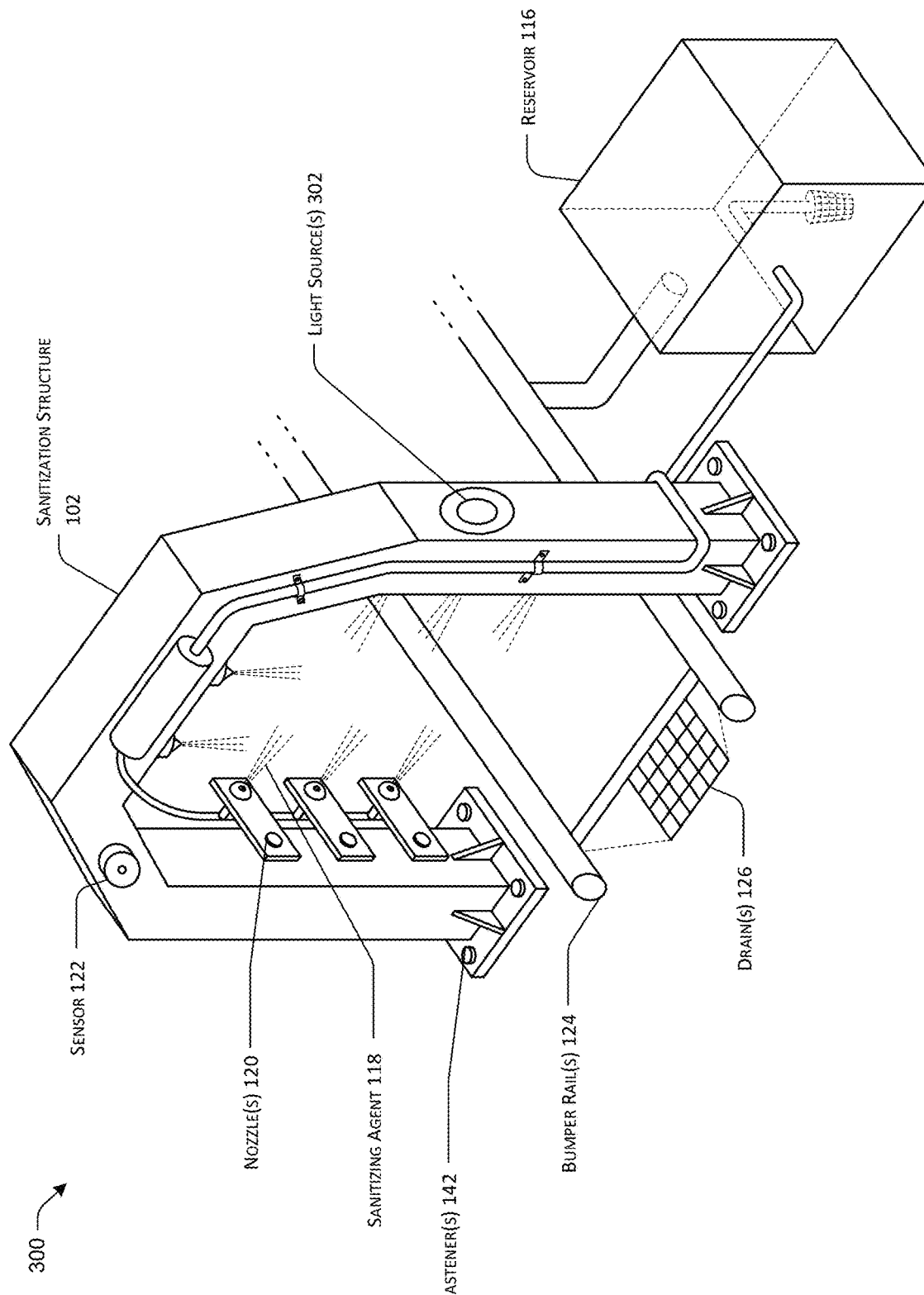
FIG. 3 is a pictorial diagram of an illustrative system that includes a sanitization structure to facilitate application of a sanitizing agent to one or more objects.

FIG. 3 is a pictorial diagram 300 of an illustrative system that includes a sanitization structure 102 to facilitate application of a sanitizing agent 118 to one or more objects 110. As shown, the sanitization structure 102 may be coupled to a reservoir 116 and one or more nozzles 120. As shown, the one or more nozzles 120 appear to be coupled to an inside side of the sanitization structure 102. The one or more nozzles 120 may be arranged on the inside side of the sanitization structure 102 to apply the sanitizing agent 118 to the entirety (e.g., each side) of an object 110. For instance, and as shown, the sanitization structure 102 appears to be depicted as having three nozzles 120 on a first inside side of an arch, two nozzles 120 on a second inside side of the arch (e.g., the top side), and three nozzles 120 on a third inside side of the arch. A position of the one or more nozzles 120 may be based on a size or a shape of the object(s) 110. In some instances, the one or more nozzles 120 may be moveable and may be coupled to the sanitization structure 102 on a track or groove such that the one or more nozzles 120 may be placed at various positions along the inside side of sanitization structure 102. The one or more nozzles 120 may also be rotatable. For instance, the one or more nozzles 120 may rotate and/or adjust while maintaining a first position along an inside surface of the sanitizations structure 102. In alternative embodiments, the sanitization structure 102 may also be configured to have one or more additional nozzles 120 that are located underneath an object 110. For instance, the sanitization structure 102 may be a loop and/or a ring with one or more additional nozzles 120 that are aimed at an underside of an object 110.

As shown, the one or more nozzles 120 appear to apply a sanitizing agent 118. The sanitizing agent 118 may be an anti-microbial solution that is composed of a chemical that removes, disables, and/or destroys pathogens. For instance, a pathogen may be a pathogenic organism that includes at least one of viruses, bacteria, fungi, protozoa, or parasites. A pathogen may be referred to as a germ. Application of the sanitizing agent 118 may also remove food products, bodily fluids, dirt, or any other substance from the object(s) 110. In various embodiments, the sanitizing agent 118 may be selected for application to the object 110 based on desired removal of a particular pathogen or pathogens. In some instances, the one or more nozzles 120 may apply a mist and/or liquid to an object 110.

As shown, the reservoir 116 appears to be coupled to the one or more nozzles 120 via a tube and/or pipe that carries a liquid (e.g., water) and/or a sanitizing agent 118 (e.g., a chemical that may or may not be combined with water). The sanitizing agent 118 may be pumped to the one or more nozzles 120 by a pressurized system that includes at least a zone control valve (or any other type of valve). As shown, a sensor 122 (e.g., a motion sensor) may detect an object 110. In response to detecting the object 110, the pressurized system may open the zone control valve allowed the sanitizing agent 118 to be applied to the object 110 via the one or more nozzles 120. As shown the sanitization structure 102 may be permanently or removably fastened to the ground (e.g., concrete) or to a surface (e.g., a platform) via fasteners 142. As shown, bumper rails 124 appear to be depicted in an opening in the sanitization structure 102 in order to guide an object 110 underneath, along an inside side, of the sanitization structure 102. As shown, a light source 302 (e.g., an indicator light) may indicate that the sanitizing agent 118 is currently being applied to the object 110 and/or the one or more nozzles 120 are currently emitting the sanitizing agent 118. In other instances, the light source 302 may turn on (e.g., emit a colored light such as a green light) in response to detecting the object 110 by the sensor 122. In some instances, the light source 302 may emit a second colored light (e.g., a yellow light) to indicate at least one of the sanitization structure 102, the drying structure 104, the UV light structure 106, and/or the UV curtain structure 108 warming-up and/or preparing for operation. The light source 302 may emit a third colored light (e.g., a red light) to indicate a failure (e.g., a mechanical and/or electrical failure) in the system. The red light may also indicate a maintenance need of one or more of the structures. For instance, the red light may indicate that an air purifier 130 coupled the drying arch 104 needs to be replaced due to it being defective.

As show, a drain 126 appears to be depicted underneath, or proximal, to the sanitization structure 102. Although any number of drains 126 are contemplated herein, the drain 126 may be configured to capture liquid run-off, or sanitization agent 118 run-off, after and/or during application to the object 110 by the one or more nozzles 120. In some instances, the drain 126 may be coupled to the reservoir 116 to recycle and/or reuse the sanitizing agent 118 for application to subsequent objects 110. In some instances, the drain 126 may include a funnel and/or a grated floor. In some instances, the drain 126 may include a basin or collection tank that is configured to store excess sanitizing agent 118, or sanitizing agent 118 that has yet to be applied to the object(s) 110.

Figure 4A:
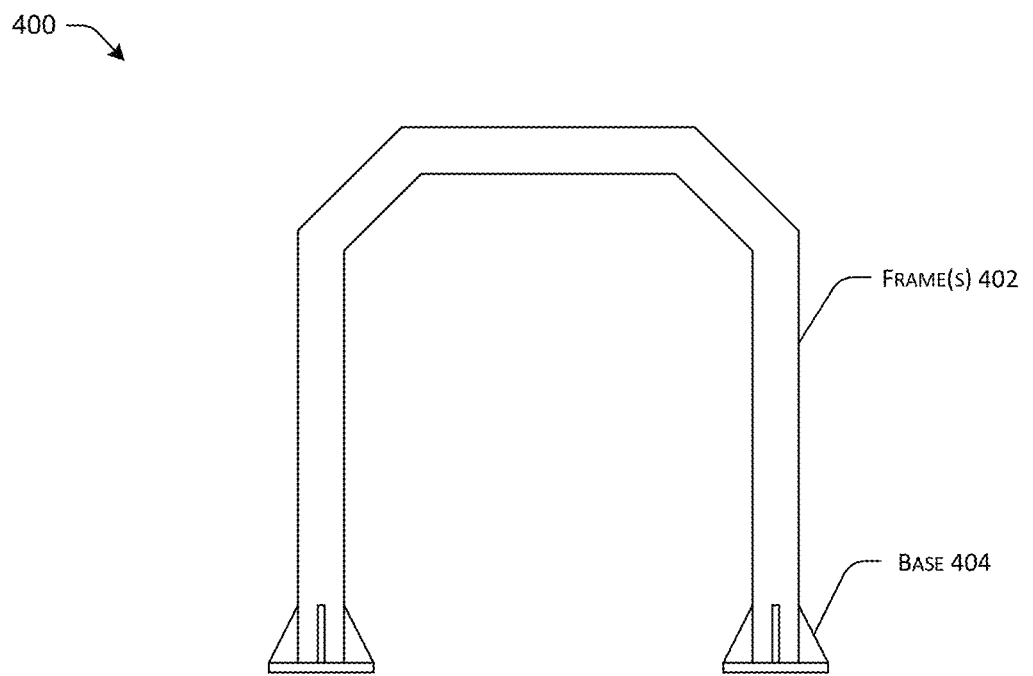
FIG. 4a is a pictorial diagram of an illustrative system that includes a frame and a base of a structure that facilitates sanitization of one or more objects.

FIG. 4a is a pictorial diagram 400 of an illustrative structure of the sanitization system 100 that includes a frame and a base of the structure. The sanitization structure 102, drying structure 104, the UV light structure 106, and the UV curtain structure 108 may include a frame 402. The frame 402 may be a structural frame that incorporates at least columns, arches, and/or beams to bear weight and/or carry a load. For instance, the frame 402, with respect to the sanitization structure 102, may be configured to couple to, and carry the weight of, the one or more nozzles 120. The frame 402, may include horizontal beams, vertical beams, non-horizontal and non-vertical beams, and/or rounded beams. The frame 402 may be an arch. In some instances, the frame 402 may be a rectangular three-dimensional shape. The frame 402 may be made of a material, or multiple materials. For instance, the frame may be composed of a rigid material including metal (e.g., aluminum), wood, and/or plastic. The frame 402 may also include a base 404. The base may be configured to allow the frame 402 to be permanently or removably coupled to the ground (e.g., concrete) or a surface (e.g., a platform) via one or more fasteners 142. For instance, the base 404 may have one or more holes or openings that allow a fastener 142 to pass through to the ground/surface.

Figure 4B:
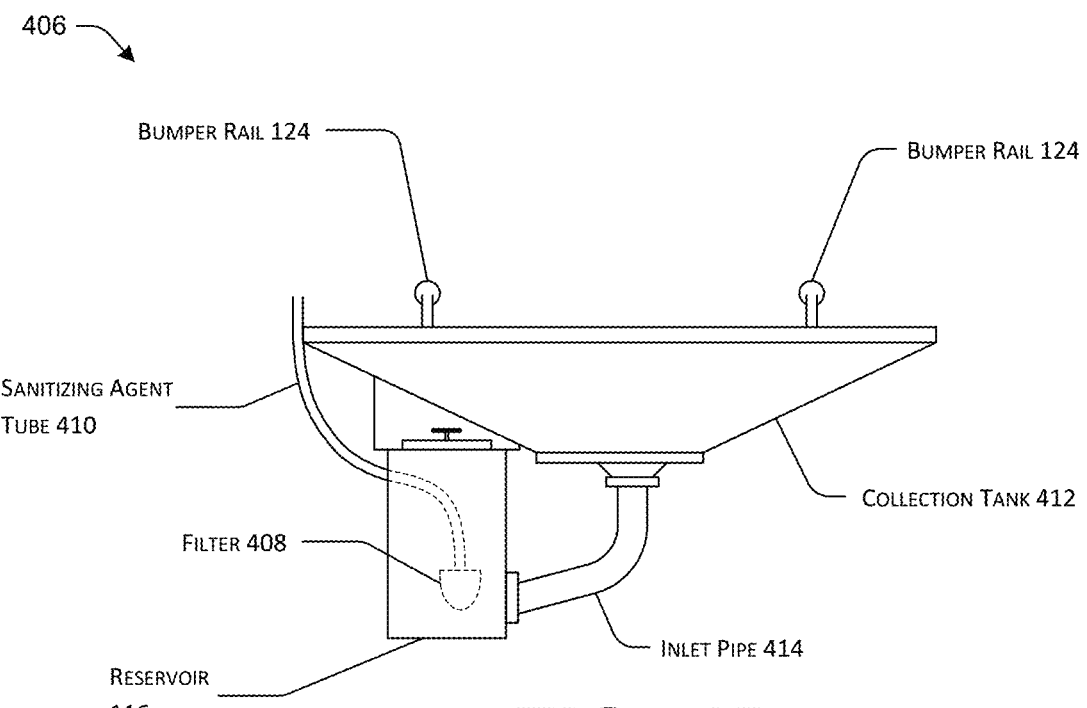
FIG. 4b is a pictorial diagram of an illustrative system that includes at least a reservoir, a filter, and a sanitizing agent tube with respect to a sanitization structure.

FIG. 4b is a pictorial diagram 406 of an illustrative apparatus that includes a reservoir 116, a filter 408, and a sanitizing agent tube 410 with respect to the sanitization structure 102. In various embodiments, the reservoir 116 may contain a solution comprised of liquid (e.g., water) and/or the sanitizing agent 118. The solution may pass through the filter 408 to remove contaminants, such as dirt. In some instances, the solution may be pumped via a pressurized system via a sanitizing agent tube 410 to the one or more nozzles 120 for application to an object 110 (e.g., a shopping cart). As shown, a collection tank 412 may be coupled to the drain 126 and/or configured to collect run-off of the sanitizing agent 118 that was applied by the one or more nozzles 120 to the object(s) 110. As shown, the collection tank appears be coupled to an inlet tube 414. The inlet tube 414 may carry, deliver, or transport the sanitizing agent 118 collected in the collection tank 412 to the reservoir 116.

Figure 5:
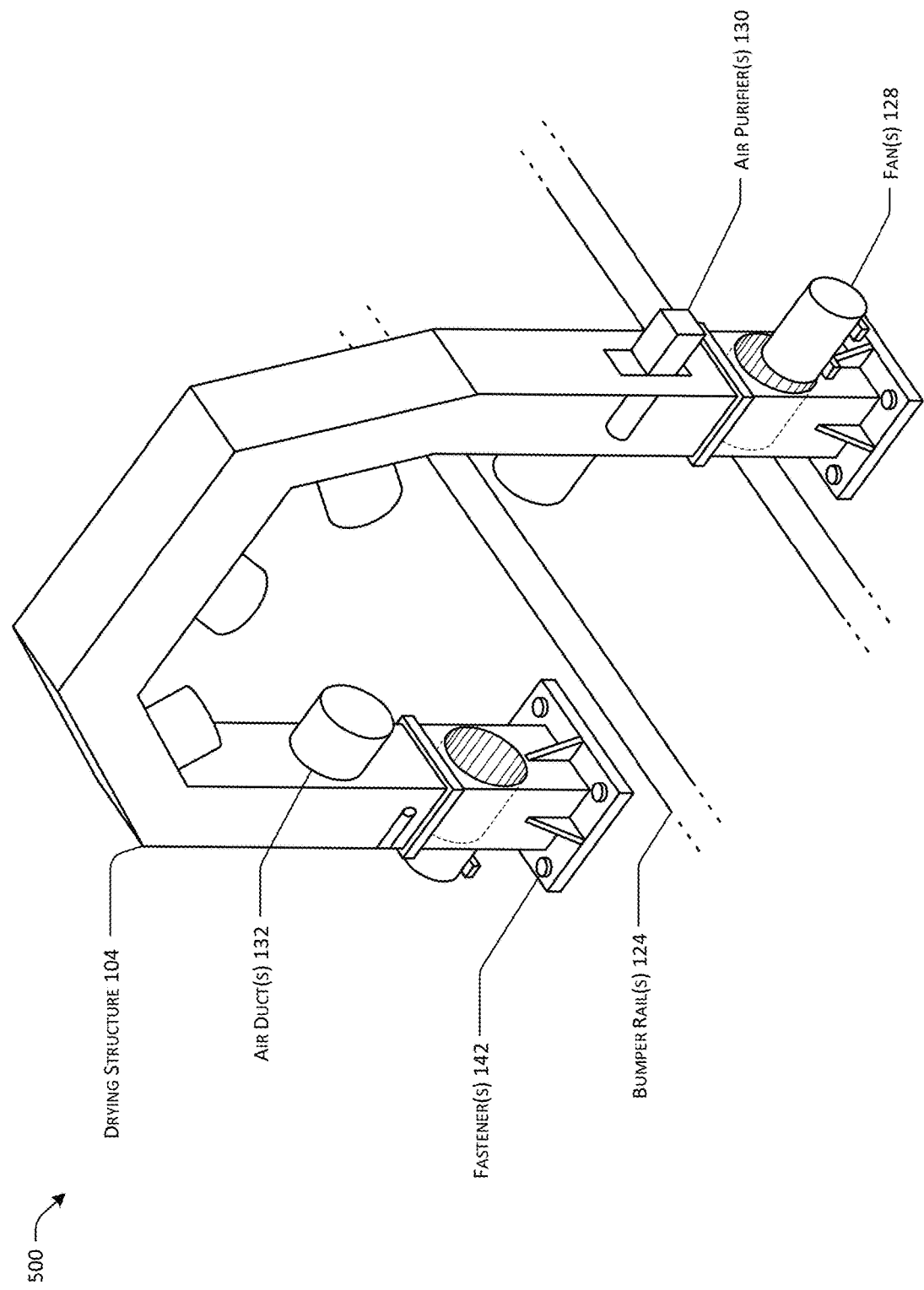
FIG. 5 is a pictorial diagram of an illustrative system that includes a drying structure to facilitate application of a gas current to one or more objects.

FIG. 5 is a pictorial diagram 500 of an illustrative apparatus that includes a drying structure 104 to facilitate application of a gas current to one or more objects 110. As shown, the drying structure 104 appears to be coupled to one or more fans 128. The one or more fans 128 may be a high-pressure blower with a minimum and maximum revolutions per minute (RPM). The one or more fans 128 may be enclosed in cages for protection purposes. In some instances, the one or more fans 128 may collect or draw gas (e.g., air) from the atmosphere. The one or more fans 128 may include one or more RPM settings (e.g., a maximum setting of 3600 RPM). The one or more fans 128 may provide a gas to the one or more air purifiers 130 or air scrubbers for purification. The one or more air purifiers 130 may convert unpurified gas (e.g., air) into purified gas (e.g., air with contaminants and/or dust particles removed). The one or more air purifiers 130 may utilize UV ozone purification. For instance, unpurified air may be infused with colony fighting organisms that disable airborne bacterial organisms. The one or more air purifiers 130 and the one or more fans 128 may provide a gas current (e.g., purified air), to the one or more air ducts 132. As shown, the drying structure 104 may be coupled to one or more air ducts 132 that apply a gas current to the object(s) 110 (e.g., the shopping cart). As shown, the one or more air ducts 132 appear to be arranged along an inside side of the drying structure 104.

As shown, the drying structure 104 appears to be coupled to five air ducts 132. A position of the one or more air ducts 132 may be based on a size or a shape of the object(s) 110. In some instances, the one or more air ducts 132 may be coupled to the drying structure 104 on a track or groove such that the one or more air ducts 132 may be moved and placed at various positions on the drying structure 104.

At least one air duct 132 of the one or more air ducts 132 may be configured to have an adjustable opening (e.g., an adjustable diameter and/or cross-sectional area). For instance, an opening of the at least one air duct 132 may have a default opening configuration to apply a gas current at a first speed. The default opening configuration may include an opening (i.e., to apply a gas current to the object 110) that is a first cross-sectional area. The opening of the at least one air duct 132 may be adjusted to have a high-speed opening configuration with a second cross-sectional area that is smaller than the first cross-sectional area. In various embodiments, a plurality of air ducts 132 may be arranged to create an air curtain. For instance, a first air duct 132 may be configured to apply a first gas current at a first angle, a second air 132 duct may be configured to apply a second gas current at a second angle, and a third air duct 132 may be configured to apply a third gas current at a third angle such that the first gas current, the second gas current, and the third gas current at last partially intersect, thereby allowing the gas current to make contact with each surface of the object(s) 110. In alternative embodiments, the drying structure 104 may also be configured to have one or more additional air ducts 132 that are located underneath an object 110. For instance, the drying structure 104 may be a loop and/or a ring with one or more additional air ducts 132 that may be aimed at the underside of an object 110. The drying structure 104 may be permanently or removably fastened to the ground (e.g., concrete) or a surface (e.g., a platform) via one or more fasteners 142. As shown, bumper rails 124 appear to be configured to provide a guide for an object(s) 110 to pass through and/or underneath the drying structure 104.

In various embodiments, one or more fans 128, the one or more air purifiers 130, and the one or more air ducts 132 may be connected and/or coupled together via a purification tunnel. A purification tunnel may be a pipe and/or tube that facilitates the movement of a gas (e.g., air) between the one or more fans 128, the one or more air purifiers 130, and the one or more air ducts 132.

Figure 6:
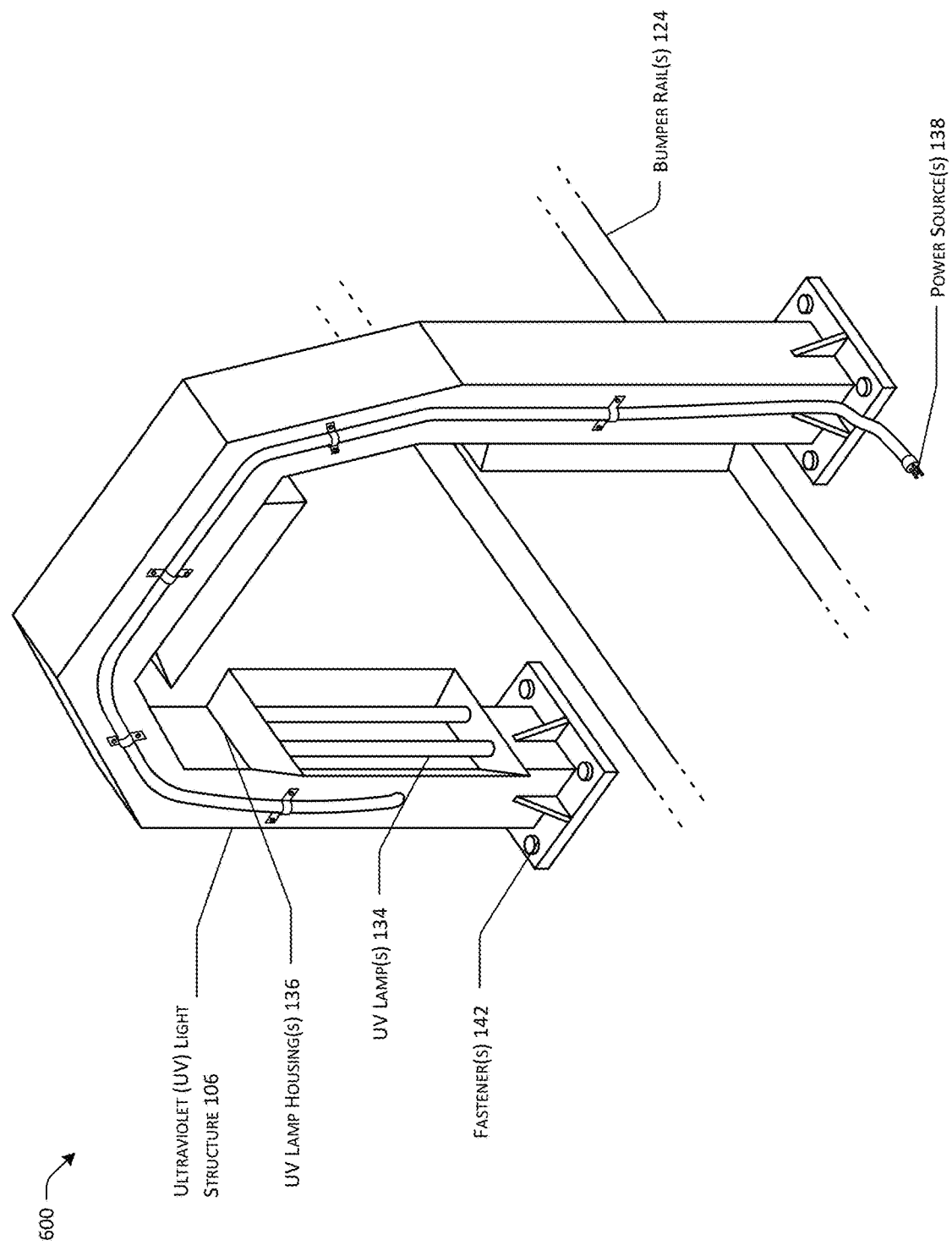
FIG. 6 is a pictorial diagram of an illustrative system that includes an ultraviolet (UV) light structure to facilitate application of UV light to one or more objects.

FIG. 6 is a pictorial diagram 600 of an illustrative system that includes an ultraviolet (UV) light structure 106 to facilitate application of UV light to one or more objects 110. As shown, the UV light structure 106 appears to be coupled to one or more UV lamps 134. The one or more UV lamps 134 may be housed in one or more UV lamp housings 136. The one or more UV lamp housings 136 may provide a coupling mechanism to configure the one or more UV lamps 134 to be coupled to the UV light structure 106. In addition, the one or more UV lamp housings 136 may block at least a portion of the UV light emitted from the one or more UV lamps 134. The one or more UV lamps 134 may be one or more germicidal UV lamps 134 that disable and/or destroy pathogens (e.g., bacteria, fungi, protozoa, viruses, and/or parasites). A first UV lamp 134 of the one or more UV lamps 134 may include a first UV setting (e.g., UV-C with a wavelength from 100 nm to 280 nm), a second UV lamp 134 may include a second UV setting (e.g., UV-B with a wavelength from 280 nm to 315 nm), and/or a third UV lamp 134 may include a third UV setting (e.g., UV-A with wavelength from 315 nm to 400 nm). The UV light structure 106 may be permanently or removably fastened to the ground (e.g., concrete) or a surface (e.g., a platform) via one or more fasteners 142. In various embodiments, the one or more UV lamps 134 may emit UV light that has a wavelength between ten and 400 nanometers. The application of UV light to an object 110 may disable and/or destroy pathogens (e.g., bacteria). For instance, UV light may be electromagnetic radiation that is mutagenic (i.e., alters the genetic material or deoxyribonucleic acid (DNA) of bacteria). In some instances, the UV light may break the molecular bonds of microorganismal DNA. As shown, bumper rails 124 appear to be configured to provide a guide for the object(s) 110 to pass through and/or underneath the UV light structure 106.

Figure 7:
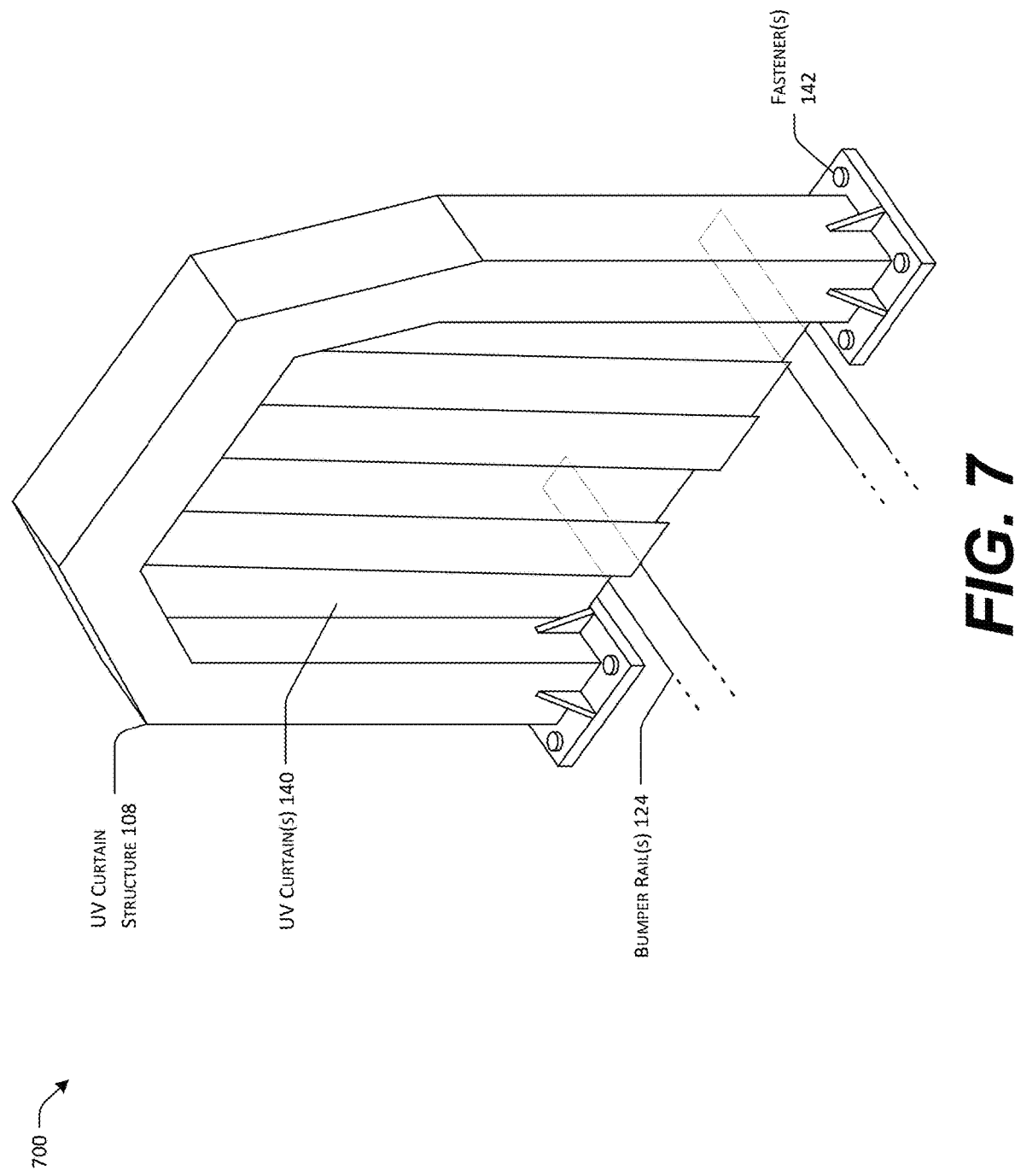
FIG. 7 is a pictorial diagram of an illustrative system that includes a UV curtain structure to facilitate blocking UV light applied by a UV light structure.

FIG. 7 is a pictorial diagram 700 of an illustrative apparatus that includes a UV curtain structure 108 to facilitate blocking UV light. As shown, the one or more UV curtain 140 may be composed of a material that blocks UV light. For instance, the one or more UV curtains 140 may be composed of an amber-tinted poly-vinyl chloride material that is able to block at least a portion of the UV light emitted from the one or more UV lamps 134. As shown, the one or more UV curtains 140 appear to be depicted as a curtain with slits that allow an object 110 to pass through. Alternatively, the one or more UV curtains 140 may be a single curtain. The UV curtain structure 108 may be permanently or removably fastened to the ground (e.g., concrete) or a surface (e.g., a platform) via one or more fasteners 142. As shown, bumper rails 124 appear to be configured to provide a guide for the object(s) 110 to pass through and/or underneath the UV curtain structure 108.

Figure 8:
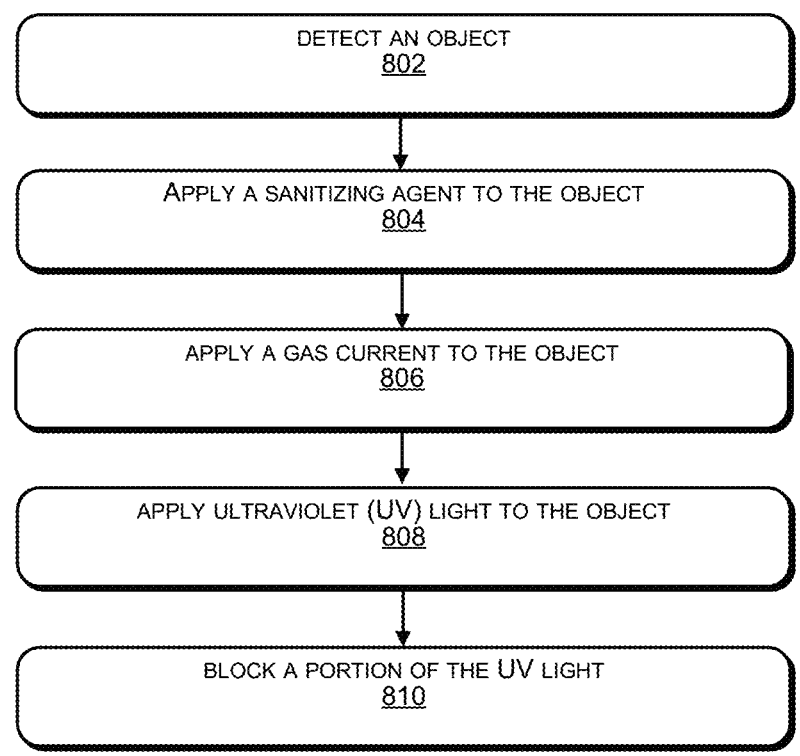
FIG. 8 is a flow diagram illustrating an example process for sanitizing one or more objects.

FIG. 8 is a flow diagram 800 illustrating an example process for sanitizing an object. For the purposes of this discussion, the operations illustrated in FIG. 8 may be performed by at least the sanitization structure 102, the drying structure 104, the UV light structure 106, and/or the UV curtain structure 108.

Block 802 illustrates detecting an object (e.g., a shopping cart, a hospital bed, a wheelchair, etc.). For instance, one or more sensors 122 (e.g., a motion sensor), may detect the object 110 at an entrance side 112 of at least one of the sanitization structure 102, the drying structure 104, the UV light structure 106, or the UV curtain structure 108. In some instances, the object(s) 110 may be configured to transmit a signal that may be received by the sensor(s) 122.

Block 804 illustrates applying a sanitizing agent to the object. The sanitizing agent 118 may be applied to the object(s) 110 via one or more nozzles 120 coupled to the sanitizing structure 102. In various embodiments, the sanitizing agent 118 may apply a mist to the object(s) 110. In some instances, the sanitizing agent 118 may be applied to the object(s) 110 in response to detecting the object(s) 110 via the sensor(s) 122. The one or more nozzles 120 may be configured to apply a continuous stream to the object(s) 110. A configuration of the one or more nozzles 120 may be based on a size or shape of the object(s) 110. The sanitizing agent 118 may be a chemical that is configured to remove, destroy, and/or disable various pathogens (or any other substance, such as food products, bodily fluids, dirt, etc.).

Block 806 illustrates applying a gas current to the object. A gas current (e.g., purified air) may be applied to the object(s) 110 via one or more air ducts 132 coupled to the drying structure 104. In various embodiments, the gas current may be obtained by drawing in air from the atmosphere via one or more fans 128 coupled to the drying structure 104 and purifying the air via one or more air purifiers 130 coupled to the drying structure 104. A configuration of the one or more air ducts 132 may be based on a size or shape of the object(s) 110. The one or more air ducts 132, the one or more air purifiers 130, and the one or more fans 128 may be connected via a pipe and/or tube.

Block 808 illustrates applying UV light to the object. UV light may be applied to the object(s) 110 via one or more UV lamps 134. The one or more UV lamps 134 may emit germicidal UV light that disables or destroys one or more pathogens. In various embodiments, the one or more UV lamps 134 may be coupled to the UV light structure 106 directly or indirectly via one or more UV lamp housings 136.

Block 810 illustrates blocking at least a portion of the UV light emitted by one or more UV lamps. In various embodiments, one or more UV light curtains 140 may be composed of a material that is able to block at least a portion of the UV light emitted by the one or more UV lamps 134. That way, potentially harmful UV light that is emitted by the UV lamp(s) 134 may not be exposed to individuals in proximity to the sanitization system 100, or the UV curtain(s) 140 may at least minimize the amount of UV light that escapes the sanitization system 100.

Figure 9:
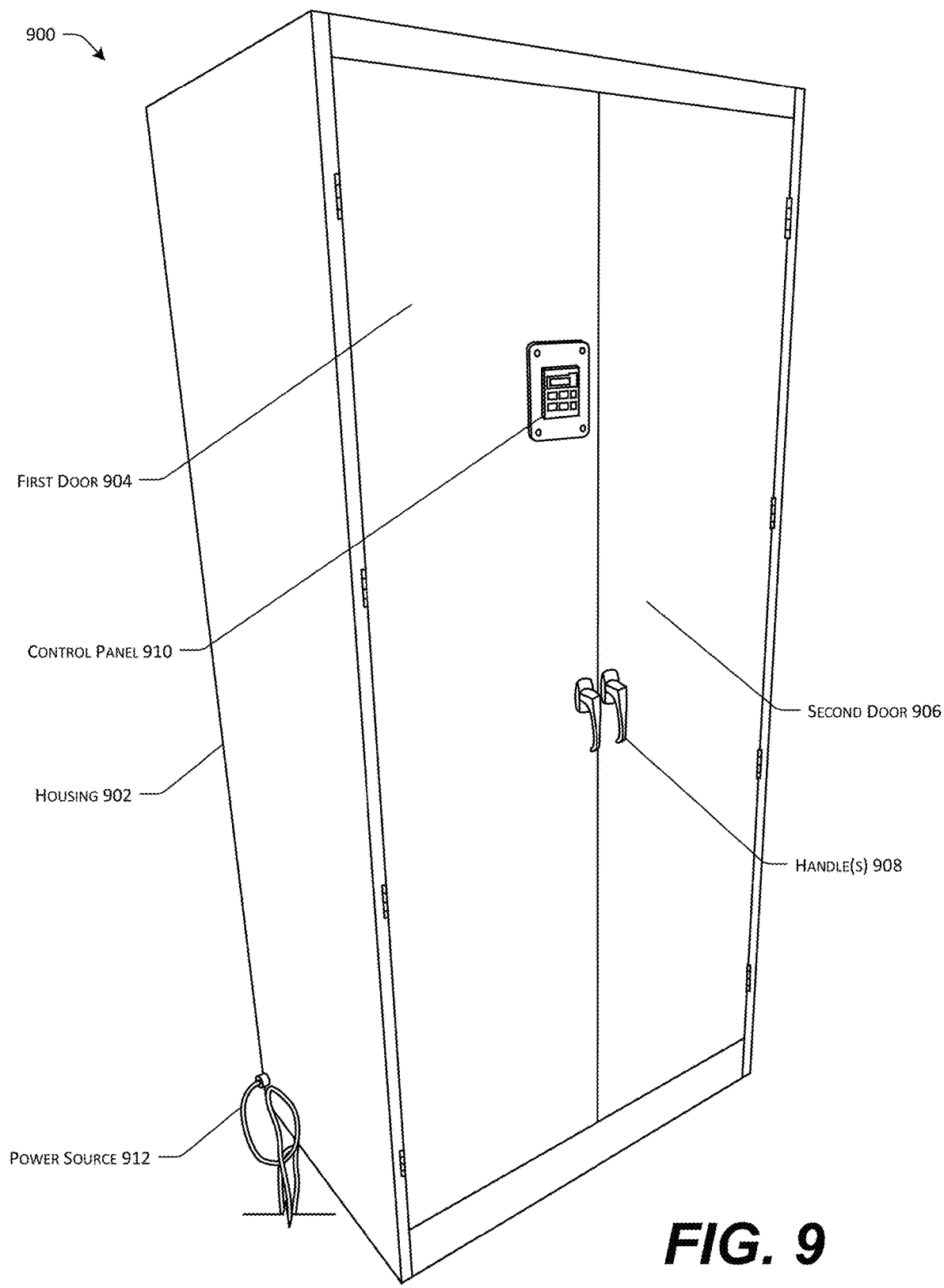
FIG. 9 is a pictorial diagram of an illustrative system that uses light to sanitize and/or disinfect an object, where the illustrative system includes one or more doors in a closed configuration.

FIG. 9 is a pictorial diagram of an illustrative apparatus 900 used to sanitize and/or disinfect objects using one or more lighting components, such as UV lamps, UVC lamps, or any other light source having a frequency or wavelength that is able to sanitize/disinfect the objects, as well as neutralize any scent associated with the objects. For the purpose of this discussion, the apparatus 900 may also be referred to as a disinfection or sanitization locker or a disinfection or sanitization cabinet. Although the apparatus 900 may be of any size (e.g., height, width, length, etc.), in some embodiments, the apparatus 900 may be approximately six fee tall and two to three feet wide or deep. The apparatus 900 may be located in any type of location or facility in which objects are to be sanitized, such as hospitals and other medical buildings, police stations, fire departments, detention centers, jails, prisons, holding rooms, intake rooms, and so on. As a result, the apparatus 900 may sanitize/disinfect any type of objects, such as clothing (e.g., inmate clothing, uniforms, scrubs or other medical clothing, etc.), gear (e.g., tactical gear, riot gear, firefighting gear, helmets, etc.), PPE (e.g., face masks, face shields, gloves, headwear, goggles, etc.), and so on.

As shown, the apparatus includes a housing 902 that encloses an interior cavity of the apparatus 902. The housing 902 may be made of any material, such as any type of metal, wood, plastic, any synthetic or semi-synthetic polymer material, or any other suitable rigid material. In the embodiment depicted in FIG. 9, the apparatus 902 may have two doors—a first door 904 and a second door 906. However, for the purposes of this discussion, the apparatus 900 may have a single door, or any number of doors, windows, or other openings. Moreover, the doors of the apparatus 900 may be situated on any surface of the apparatus 902, and the doors may traverse the entire width, length, or depth of the housing 902, or only a portion thereof. The first door 904 and/or the second door 906 may be used to access the interior cavity of the apparatus 900. Once the doors have been opened, an object to be sanitized may be placed within the apparatus 900. As shown in FIG. 9, each of the first door 904 and the second door 906 contain a handle 908, although only one of the doors may include a handle 908. The handles 908 may be used to open the first door 904 and/or the second door 906 via hinges in order to access the interior cavity of the apparatus 900. As shown, FIG. 9 depicts the first door 904 and the second door 906 being in a closed state/configuration.

At any location on the housing 902, the apparatus 900 may include a control panel 910 that is used to control operations associated with the apparatus 900. In FIG. 9, the control panel 910 is shown being located on the first door 904. The control panel 910 may be affixed to the housing 902 and include a user interface (or a graphical user interface), one or more buttons, sliders, levers, switches, etc. Using the control panel 910, a user may open/close the doors, turn on/off the lighting components within the interior cavity of the apparatus 900, specify a duration in which the lighting components are to be on, adjust a frequency or wavelength of light emitted by the lighting components, and so on. That is, using the control panel 910, a user may cause the lighting components to emit light for a particular period of time that will sanitize and disinfect the one or more objects that are within the interior cavity of the apparatus 900. In an alternative embodiment, the apparatus 900 may be controlled by means other than the control panel 910, such as a remote control or a mobile application residing on a device (e.g., a mobile telephone, a tablet device, a desktop/laptop computer, etc.). Or, the control panel 910 may be separate from the apparatus 900, but be connected to the apparatus 900 via one or more electrical wires or be connected wirelessly (e.g., WiFi, Bluetooth, cellular connection, etc.). A power source 912 may also be included to provide power (e.g., electricity) to the lighting components and/or the control panel 910. The power source may be a plug that is inserted into an outlet for electrical power. However, in other embodiments, the apparatus may be operated using other types of power, including a battery, solar power, a gas or diesel engine, propane, etc.

Figure 10:
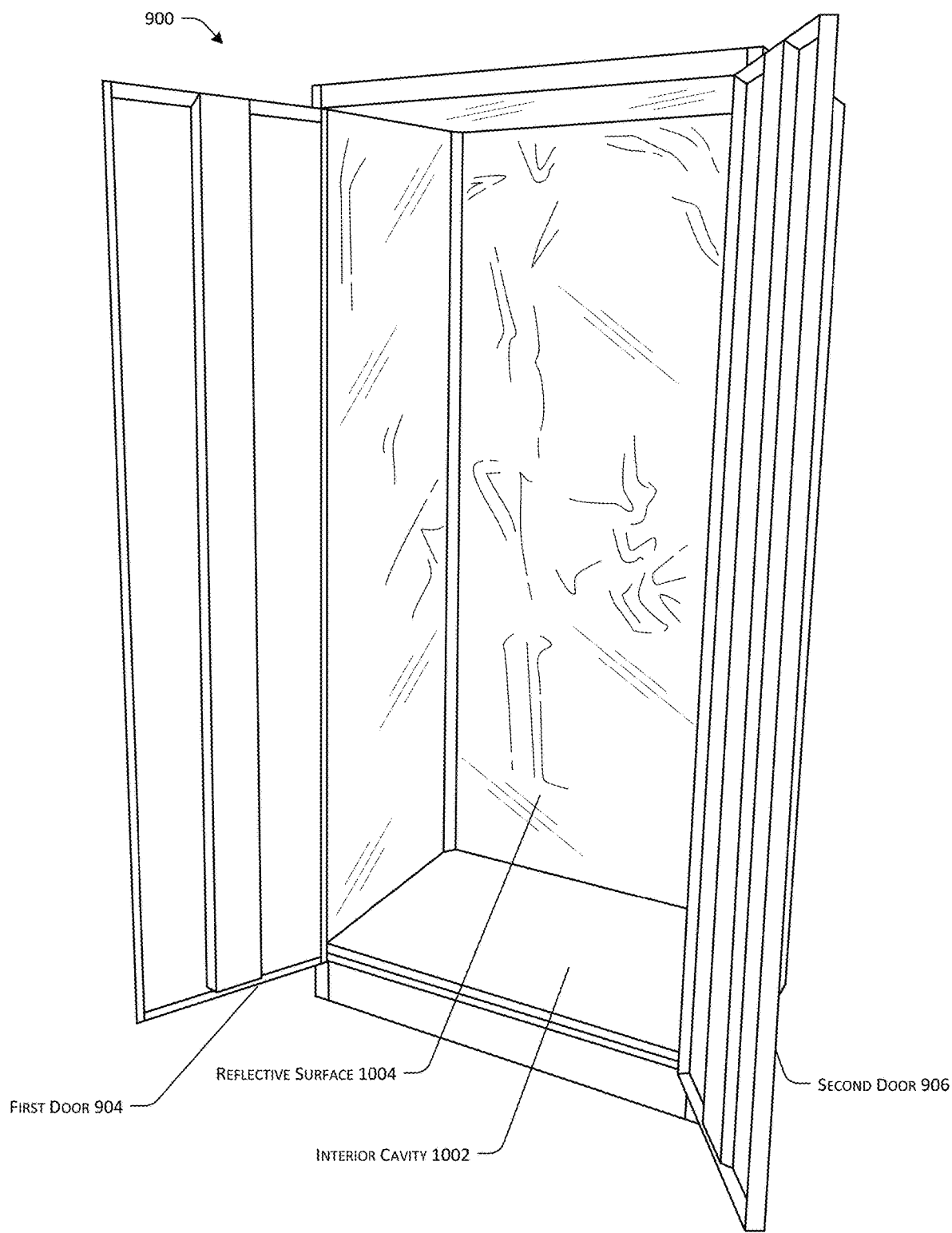
FIG. 10 is a pictorial diagram of the illustrative system depicted in FIG. 9, where the one or more doors are in an open configuration.
Figure 11:
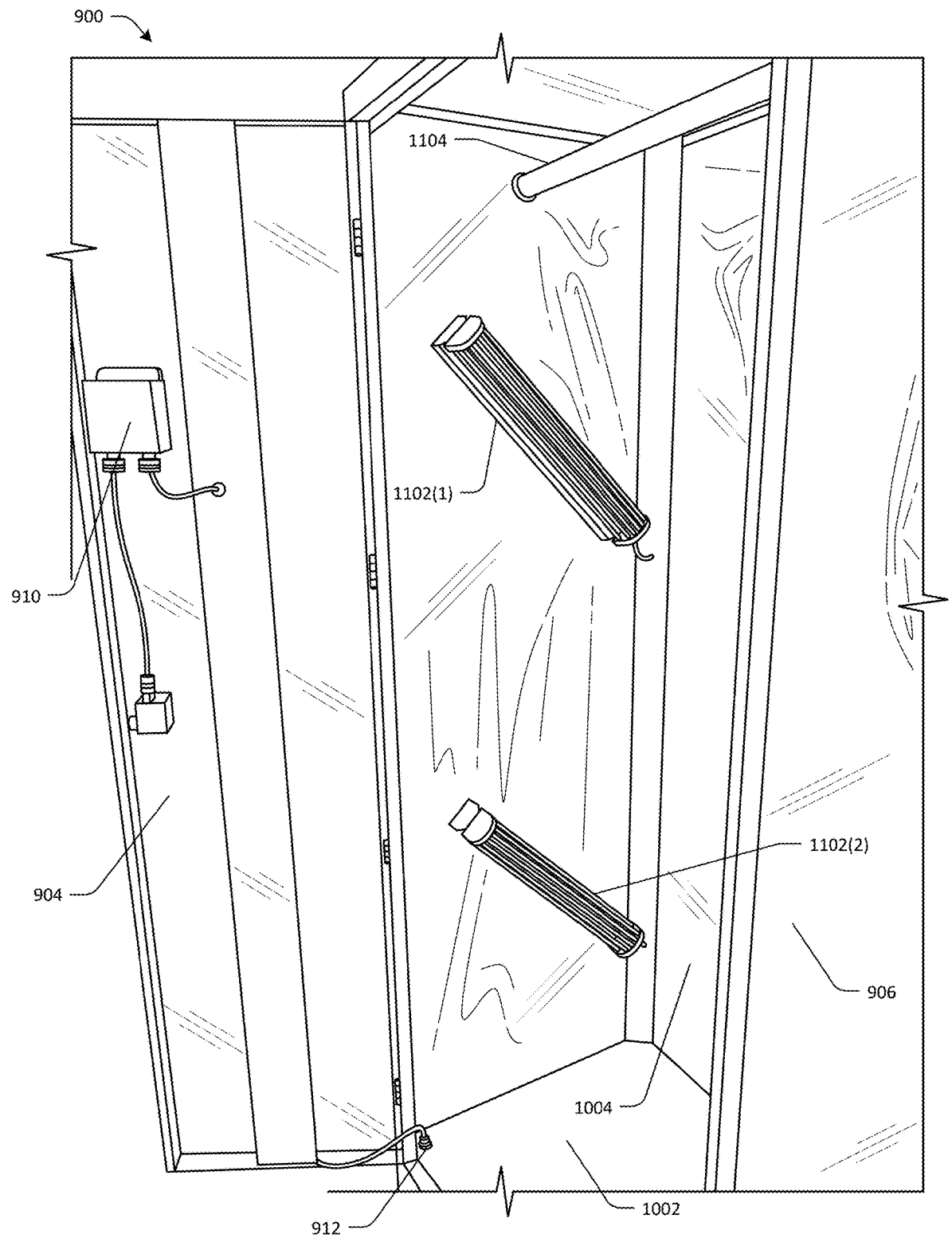
FIG. 11 is a pictorial diagram of the illustrative system depicted in FIG. 9 that illustrates a view different than that depicted in FIG. 10, where the one or more doors are in the open configuration.

FIG. 10 is a pictorial diagram of the apparatus illustrated in FIG. 9. As shown, the first door 904 and the second door 906 of the apparatus 900 are in an open state/configuration such that the interior cavity 1002 of the apparatus 900 is visible and accessible. One or more walls within the interior cavity 1002 of the apparatus 900 include a reflective surface 1004. Although the lighting components are not shown in FIG. 10 (they are depicted in FIG. 11), the reflective surfaces 1004 reflect light emitted by the lighting components such that all surfaces of an object included within the apparatus 900 are exposed to the light. For instance, provided that a user places an object within the apparatus 900, closes the doors, and activates the lighting components via the control panel 910, the light may be emitted by the lighting components and continuously reflected by the reflective surfaces 1002 towards the object(s) and the different interior walls, the inner bottom surface, and the inner top surface within the interior cavity 1002. As a result, all surfaces of the object will be sanitized/disinfected by the light emitted by the lighting components. The interior walls may be made up of the reflective surface 1004 or the reflective surface 1004 may be affixed to the interior walls in some manner (e.g., adhesive, screws/nails/clips, welded, etc.). Moreover, a single interior wall (including the interior surface of either of the doors), multiple interior walls, or each of the interior walls may include the reflective surface 1004. It is also contemplated that the inner surface of the ceiling and/or the inner surface of the floor within the interior cavity 1002 may or may not have the reflective surface 1004.

The reflective surface 1004 may be included within the interior surfaces of any or each of the apparatus depicted in FIGS. 9-24, and the reflective surface 1004 may be any type of metal or any type of polyester film having a coating of metal, such as Metallized DuraLar™, which consists of a polyester film with a thin coating of aluminum. Example metals that may be used in association with the reflective surface 1004 may include aluminum, mild steel, stainless steel, nickel, silver, chrome plated steel, anodized aluminum, aluminum foil, or any other type of metal. The reflective surface 1004 may also be stainless steel sheet metal with a brushed reflective surface finish. Other types of materials that may be used in association with the reflective surface 1004 may include Mylar®, high-density polyethylene with a reflective coating, metal mirrors, glass mirrors, acrylic mirrors, polycarbonate mirrors, and/or polished sheet metal made up of any of the types of metals referenced above. Although many types of materials have been described in this paragraph, as well as throughout this disclosure, it is contemplated that any type of material that reflects or redirects light can be used in association with the interior surfaces within the apparatus depicted in FIGS. 9-24.

FIG. 11 is a pictorial diagram of the apparatus 900 illustrated in FIGS. 9 and 10. As shown, the doors of the apparatus 900 are in the open state/configuration such that the interior cavity 1002 of the apparatus 900 is visible and accessible. Also shown are the back sides of the first door 904 and the second door 906, the back side of the control panel 910, the power source 912, and the reflective surfaces 1004 of the interior walls of the interior cavity. The interior cavity 1002 of the apparatus 900 may include one or more lighting components 1102(1) and 1102(2). As discussed herein, the lighting components 1102 may emit light (e.g., UV light, UVC light, etc.) that sanitizes/disinfects objects within the interior cavity of the apparatus 900. As referenced with respect to FIG. 10, the reflective surfaces 1004 within the interior cavity 1002 may reflect the light such that the light sanitizes/disinfects as many surfaces of the object as possible. The lighting components 1102 may be of any number and may be situated at any location within the interior cavity 1002, such as on the interior walls, the back side of the doors, the ceiling, and/or the floor.

The lighting components 1102 referenced throughout this disclosure may include ultraviolet (UV) lights, ultraviolet-C (UVC) lights, or any other type of light that emits light (e.g., UV light, UVC light, etc.) that is sufficient to eliminate or destroy pathogens, bacteria, viruses, and so on. The size of the lighting components 1102 may vary such that the frequency and intensity of light output can be adjusted. That is, the size, type, and position of the lighting components 1102 may vary to emit light of a sufficient intensity at varying wavelengths. An example wavelength may be 254 nanometers, which is highly damaging to nucleic acids and other pathogens, viruses, bacteria, etc., when they are exposed to light having that particular wavelength. However, other wavelengths of light may also be utilized to disinfect and/or sanitize objects that are exposed to the light. The duration or amount of light emitted towards an object to disinfect the object may be dependent upon the variance of the lighting components (e.g., size, type, distance between lighting components and object, etc.).

The interior cavity 1002 may include any structural component 1104 in which the object(s) can be placed upon, hung from, draped over, etc., and the type of structural component 1104 may be dependent upon the type of object to be sanitized. As shown in FIG. 11, the interior cavity 1002 includes a bar (or rod, rail, etc.) that can be used to hang objects to be sanitized. For instance, clothing items may be hung from (e.g., using a hanger) or draped over the bar. Any number of bars may be included within the interior cavity 1002 and the bar(s) may be placed at any location, orientation, configuration, angle, etc. Other structural components 1104 that may be used hold or support the objects may include hooks, nails, or pins attached to the interior walls, doors, or ceiling, a rack (e.g., a drying rack for clothing), a platform, a shelf, and so on. Any number, size, shape, type, etc. of the structural components 1104 are contemplated herein.

In some embodiments, the lighting components 1102 may be detachably affixed within the interior cavity 1002 such that the lighting components 1102 may be moved to different locations, shifted, rotated, moved to a different angle, etc. This may allow the lighting components 1102 to be focused on the object to be sanitized based on the size, type, shape, etc. of the object. A frequency or wavelength of light emitted by the lighting components 1102 may also be adjusted (e.g., increased, decreased, etc.) prior to, or during, sanitization of the objects. The lighting components 1102 may be removed from the interior cavity 1002, or additional lighting components 1102 may be added to the interior cavity 1002. Power may be supplied to the light components 1102 by the power source 912 and/or one or more batteries.

Figure 12:
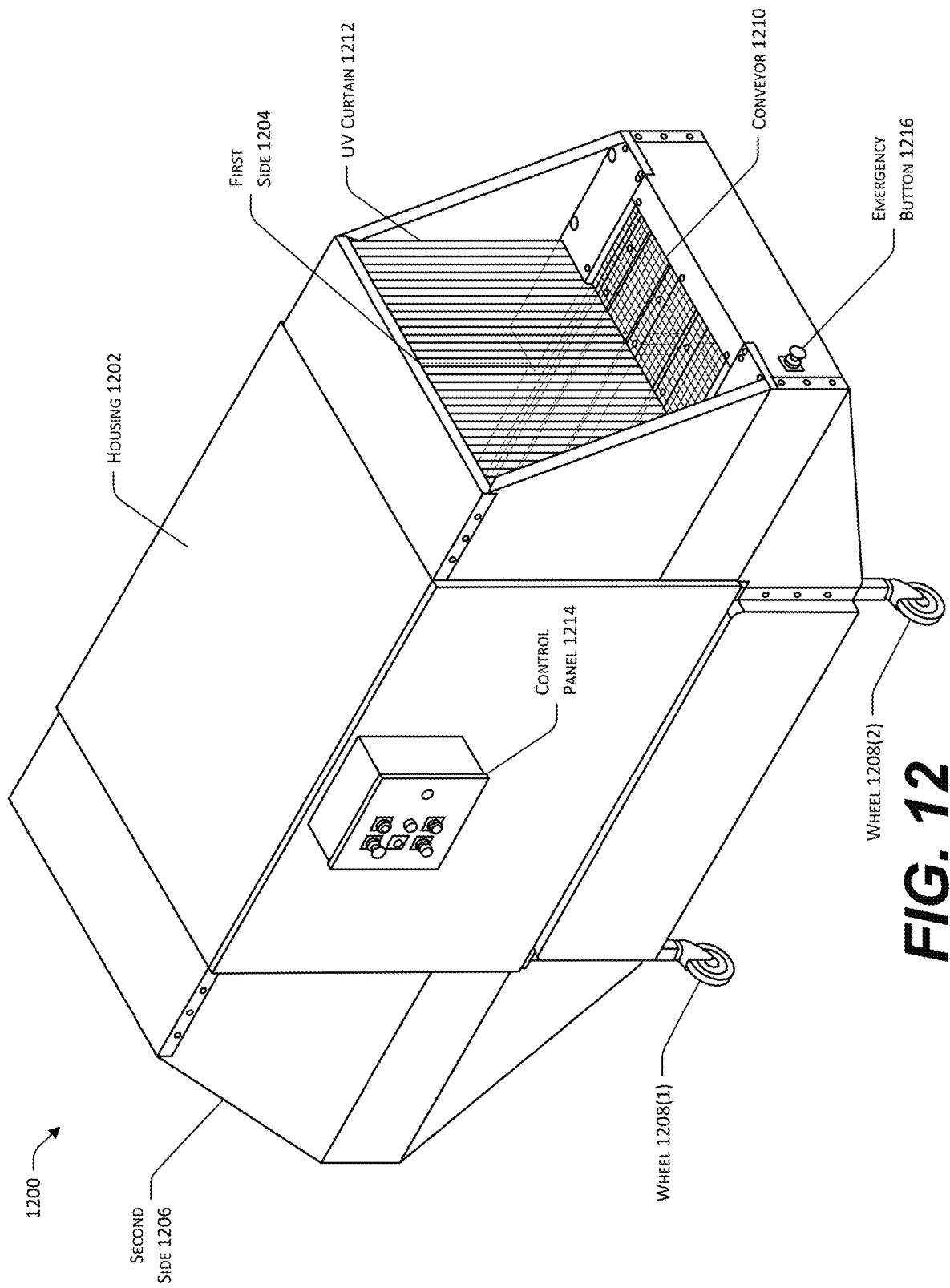
FIG. 12 is a pictorial diagram of an illustrative system that uses light to sanitize and/or disinfect an object, where the illustrative system includes a first opening, a second opening, and a conveyor to transport the object between the first opening and the second opening.

FIG. 12 is a pictorial diagram of an apparatus 1200 that is used to sanitize and disinfect objects. As will described in additional detail, the apparatus 1200 is a conveyor table system having a conveyor that passes objects through a tunnel that includes one or more lamps that emit light (e.g., UV light, UVC light, etc.) towards the objects. The light and radiation emitted by the lamps are able to destroy bacteria, viruses (including the DNA and RNA structure of viruses), and other pathogens that may be harmful to humans. The apparatus 1200 is mobile in nature and may be used as an on-demand sanitization station for individuals, entities, organizations, etc. For instance, the apparatus 1200 may be placed at entrances and/or exits to various indoor and outdoor venues, such as buildings, schools, concerts, hospitals (and other medical facilities), government buildings, stadiums, and so on. Objects that may be sanitized by the apparatus 1200 may include backpacks, handbags, PPE, electronic devices, loose clothing or other soft materials, hand-held equipment, and other objects commonly touched by people.

As illustrated in FIG. 12, the apparatus 1200 includes a housing 1202 that encapsulates the interior components of the apparatus 1200. The housing 1202 may be of any type of material, such as any type of metal (e.g., stainless steel), wood, plastic, any synthetic or semi-synthetic polymer material, or any other suitable rigid material. The housing 1202 also includes a first side 1204 and a second side 1206, wheels 1208(1) and 1208(2) (the other two wheels not shown), and a conveyor 1210, such as a conveyor belt.

In the embodiment illustrated in FIG. 12, the conveyor 1210 may move in a direction from the first side 1204 towards the second side 1206 such that an object is placed at the first side 1204 and transferred through the apparatus 1200 towards the second side 1206, where the object is removed. Lighting components (e.g., UV lamps, UVC lamps, etc.) within the housing and between the first side 1204 and the second side 1206 emit light (e.g., UV light, UVC light, etc.) toward the object as it is moving via the conveyor 1210. The object has been sanitized/disinfected once the object has passed through the apparatus 1200, and then a user may remove the object from the second side 1206 of the apparatus 1200. However, the conveyor 1210 can move in both directions such that objects enter the apparatus 1200 at the second side 1206 and are removed from the apparatus 1200 from the first side 1204. The apparatus 1200 also may or may not include wheels 1200, which may allow the apparatus 1200 to be moved/wheeled to different locations. In FIG. 12, the remaining two wheels 1208 are obscured by the housing 1202 of the apparatus 1200. As described in additional detail herein, the apparatus 1200 may include a UV curtain 1212 at the first side 1204 and/or the second side 1206 of the apparatus 1200. As described elsewhere herein, the UV curtain(s) 1212 may block/prevent light from leaving the interior of the housing 1202 since various frequencies of light can be harmful to individuals.

At any location on the housing 1202, the apparatus 1200 may include a control panel 1214 that is used to control operations associated with the apparatus 1200. In FIG. 12, the control panel 1214 is shown being located on a side surface of the housing 1202. The control panel 1214 may be affixed to the housing 1202 at any location and include a user interface (or a graphical user interface), one or more buttons, sliders, levers, switches, etc. Using the control panel 1214, a user may start or stop the conveyor 1210, turn on/off the lighting components within the apparatus 1200, adjust a speed/rate and/or direction of the conveyor 1210, adjust a frequency or wavelength of light emitted by the lighting components, and so on. That is, using the control panel 1214, a user or operator may cause the lighting components to emit light that will sanitize and disinfect the one or more objects that are passing through the apparatus 1200. In an alternative embodiment, the apparatus 1200 may be controlled by means other than the control panel 1214, such as a remote control, a mobile application residing on a device (e.g., a mobile telephone, a tablet device, a desktop/laptop computer, etc.). Or, the control panel 1214 may be separate from the apparatus 1200, but be connected to the apparatus 1200 via one or more wires, or may be connected wirelessly (e.g., WiFi, Bluetooth, cellular connection, etc.). In various embodiments, a power source may be associated with the apparatus 1200 in order to supply electric power for the lighting components, the conveyor 1210, and/or the control panel 1214. The power source may be a plug that is inserted into an outlet for electrical power. However, in other embodiments, the apparatus may be operated using other types of power, including solar, a gas or diesel engine, propane, a battery, etc.

As either part of the control panel 1214 or separate from the control panel 1214, the apparatus 1200 may include an emergency button 1216 (or switch, lever, etc.). When activated (e.g., pushed, pressed, switched, pulled, etc.), the emergency button 1216 may cause the lighting components and/or the conveyor 1210 to cease operating. For instance, if an object not intended to pass through the apparatus 1200 is found on the conveyor 1210, if one of the UV curtains 1212 breaks or fails, or if the apparatus 1200 is operating in an unintended manner, a user may push the emergency button 1216 to cause the apparatus 1200 to cease operating.

Figure 13:
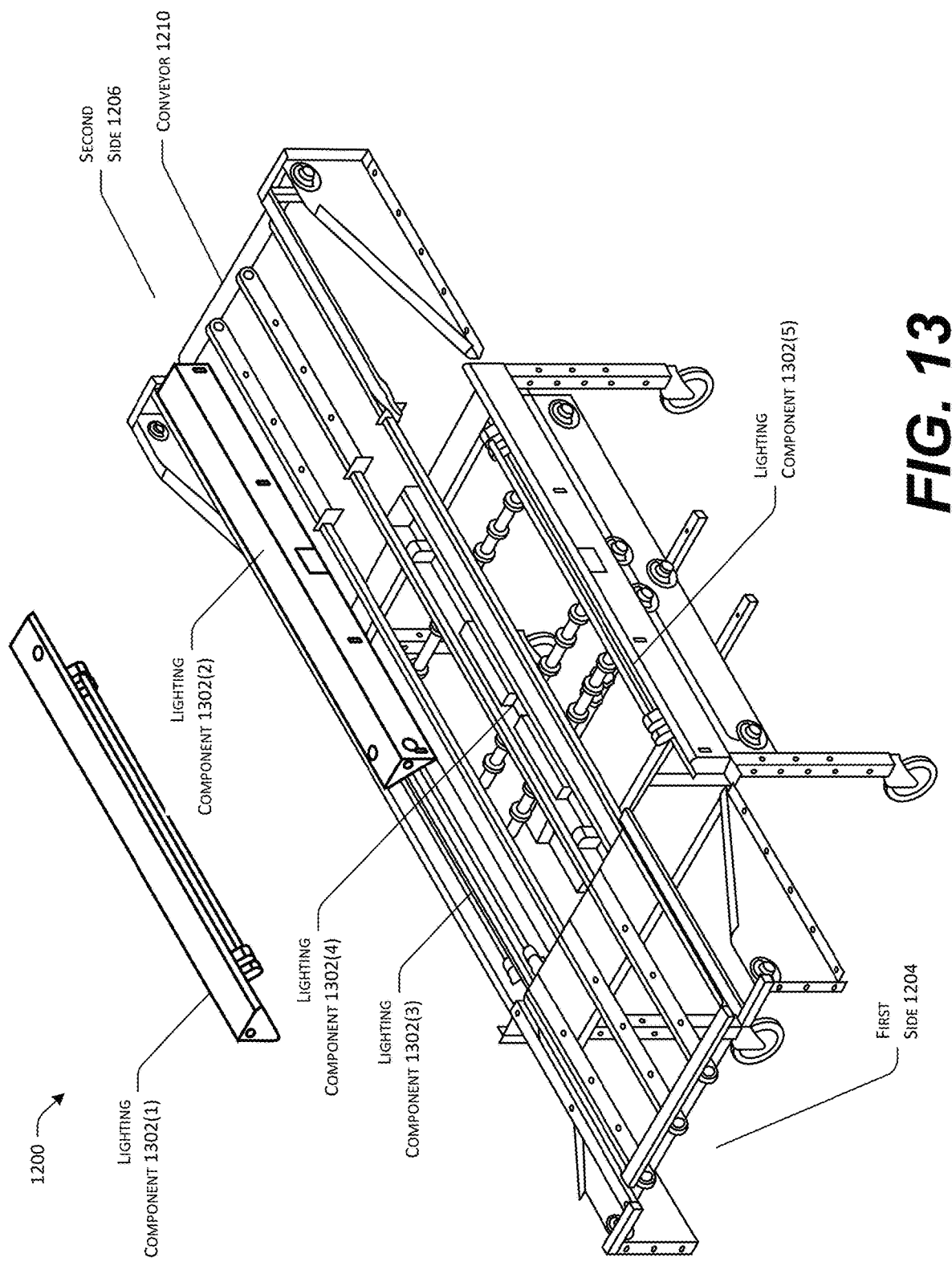
FIG. 13 is a pictorial diagram of the illustrative system depicted in FIG. 12, where the housing of the illustrative system has been removed to show the interior of the illustrative system.

FIG. 13 is a pictorial diagram of the apparatus 1200 illustrated in FIG. 12. As shown, the housing 1202 of the apparatus 1200 has been removed so that the internal/interior components of the apparatus 1200 can be seen. As in FIG. 12, the apparatus 1200 continues to have a first side 1204, a second side 1206, and a conveyor that extends from the first side 1204 to the second side 1206. For instance, when an object is placed at the first side 1204, the conveyor 1210 will transport the object though the apparatus 1200 to the second side 1206, where the sanitized object will be removed from the apparatus 1200.

The depiction of the apparatus 1200 illustrated in FIG. 12 obfuscates one or more lighting components 1302 (1302(1)-1302(5)) that are in the interior of the apparatus 1200. The lighting components 1302 may be UV lamps, UVC lamps, or any other light/lamp that emits light in a wavelength or frequency to sanitize (kill/remove pathogens, bacteria, viruses, etc.) objects. Although five separate lighting components 1302 are shown in FIG. 13, any number of lighting components 1302 are contemplated herein.

The lighting components 1302 may be situated throughout the interior of the apparatus such that light emitted by the lighting components 1302 is directed towards different surfaces of an object as the object is transported down the conveyor 1210. For instance, and as depicted in FIG. 13, lighting components 1302(1) and 1302(1) are each located adjacent to the top surface of the housing 1202 and adjacent to a side surface of the housing 1202. Such overhead lighting components 1302 allow for light to be directed towards the top and side surfaces of the object passing through the apparatus 1200. Lighting components 1302(3) and 1302(5) are located adjacent to the side surfaces of the housing 1202 and adjacent to the conveyor 1210, and lighting component 1302(4) is situated underneath the conveyor 1210 or in a gap of the conveyor 1210. Such lighting components 1302 may emit light toward the side surfaces and the bottom surface of the object passing through the apparatus 1200. In this configuration/orientation of lighting components 1302, light may be emitted by each of the lighting components 1302 such that different surfaces of the object passing through the apparatus 1200 are exposed to sanitizing/disinfecting light.

In some embodiments, the lighting components 1102 may be detachably affixed/coupled within the interior cavity 1002 such that the lighting components 1302 may be moved to different locations, shifted, rotated, moved to a different angle, etc. For instance, the lighting components 1302 may be affixed to the interior of the apparatus 1200 via rails, brackets, or any other coupling mechanism that allows the lighting components 1302 to move or allows the direction of the light emitted to be adjusted. This may allow the lighting components 1302 to be focused on the object to be sanitized based on the size, type, shape, etc. of the object. A frequency or wavelength of light emitted by the lighting components 1302 may also be adjusted (e.g., increased, decreased, etc.) prior to, or during, sanitization of the objects. The lighting components 1302 may be removed from the apparatus 1200, or additional lighting components 1302 may be added to the apparatus 1200. Power may be supplied to the light components 1302 by and the conveyor 1210 by one or more power sources.

Figure 14:
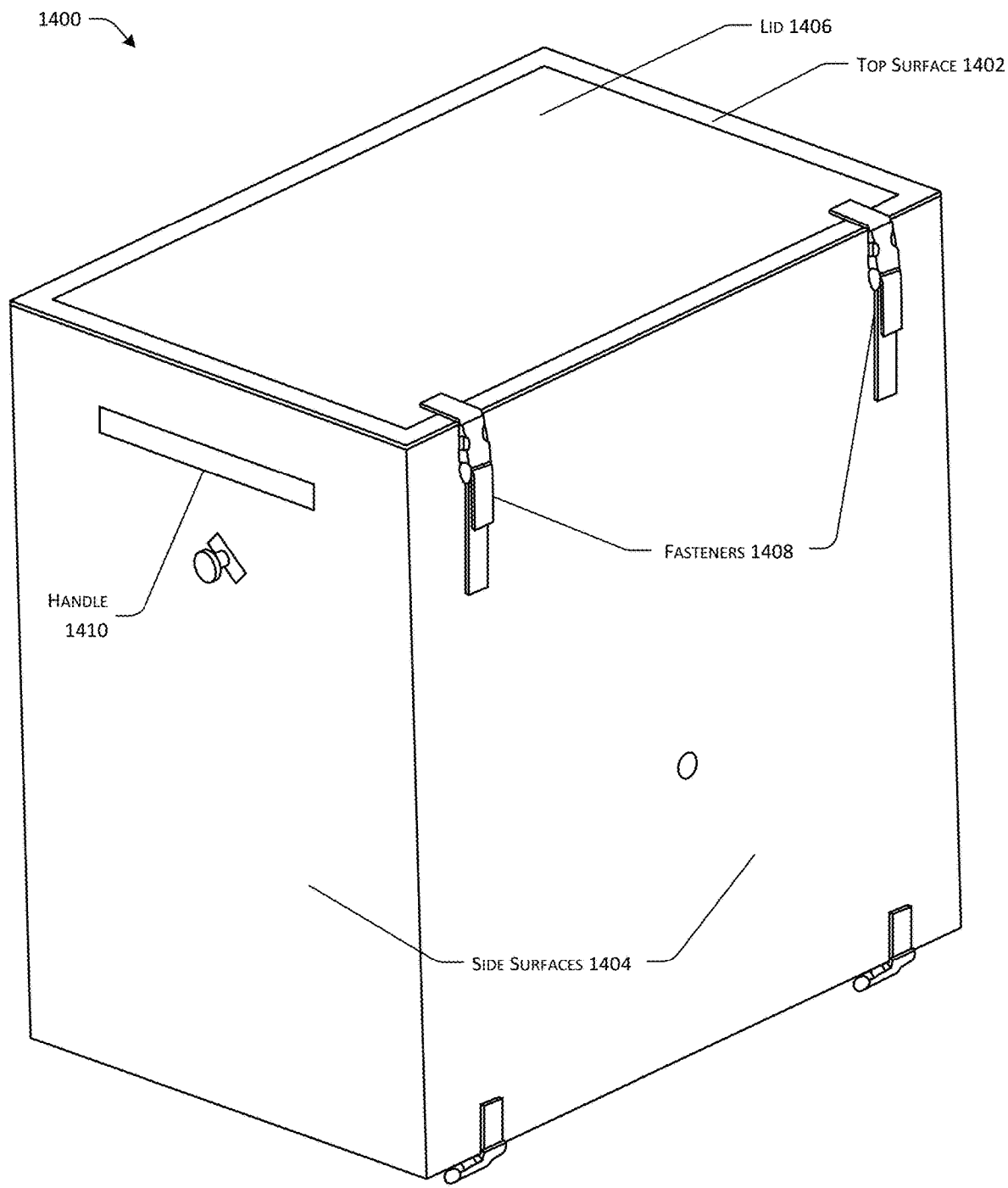
FIG. 14 is a pictorial diagram of an illustrative system that uses light to sanitize and/or disinfect an object, where the illustrative system is in an expanded state and is in a closed configuration.

FIG. 14 is a pictorial diagram of an apparatus 1400 used to sanitize one or more objects placed therein. In some embodiments, the apparatus 1400 may be a transportable bag, container, or box that uses UV light or UVC light to sanitize and disinfect objects of a smaller size. For instance, first responders, such as police officers and firefighters, are required to use different types of equipment on a daily basis and, as a result, pathogens (e.g., bacteria, protozoa, viruses, fungi, etc.) may be transferred between each other and their equipment. In order to eliminate the transfer of such pathogens, the apparatus may be kept in police cars, fire trucks, ambulances, etc. to quickly sanitize/disinfect such objects. Used and/or dirty equipment may be placed within the apparatus 1400 for a short period of time (e.g., around 30 seconds), and UV/UVC light emitted by UV/UVC lamps within the apparatus 1400 will sanitize such items. Upon being sanitized, the objects (e.g., tools, gear, medical equipment, etc.) would be immediately and safely ready for subsequent use.

As illustrated in FIG. 14, the apparatus 1400 includes a top surface 1402, multiple side surfaces 1404, a lid 1406, one or more fasteners 1408, and a handle 1410. In various embodiments, the apparatus 1400 may be made of any material, including metal, wood, plastic, fabric, or any other material that is sufficiently rigid. In other embodiments, the apparatus may be made of any type of non-rigid or semi-rigid material, such as fabric (e.g., canvas). Objects to be sanitized can be placed within the apparatus 1400, and sanitized objects can be removed the apparatus 1400, via the lid 1406. That is, the lid 1406 may be opened and closed to provide access to the interior cavity of the apparatus 1400. As shown in FIG. 1400, the lid 1406 is in the closed configuration/state.

The apparatus 1400 can be transitioned between an expanded state or configuration and an unexpanded or collapsed state/configuration. When in use (e.g., objects can be placed within the apparatus 1400 and be sanitized), the apparatus 1400 is in the expanded state/configuration. From the expanded state/configuration, the apparatus 1400 may be transitioned to the unexpanded or collapsed configuration/state, which may provide for easier or more efficient transport and storage. As illustrated in FIG. 14, the apparatus 1400 is in an expanded state. The interior cavity of the apparatus 1400 may include a collapsible structure that includes one or more lighting components (e.g., lamps) that emit light (e.g., UV light, UVC light, etc.), which sanitizes the object(s) included therein by destroying pathogens associated with the object(s). The fasteners 1408 may be any type of mechanism that causes the lid 1406 to remain closed, particularly when the apparatus 1400 is currently sanitizing one or more objects. The fasteners 1408 may include straps, buckles, zippers, Velcro®, buttons, clips, ties (e.g., string or rope), or any other mechanism that will keep the lid 1406 in the closed configuration. The handle 1410 may be disposed on any exterior surface of the apparatus 1400 and is used to hold, lift, transport, etc. the apparatus 1400, whether the apparatus 1400 is in use or not. The apparatus 1400 may have a single or multiple handles 1410, such as two handles 1410 disposed on opposite sides of the apparatus such that the apparatus 1400 may be carried using two hands.

Figure 15:
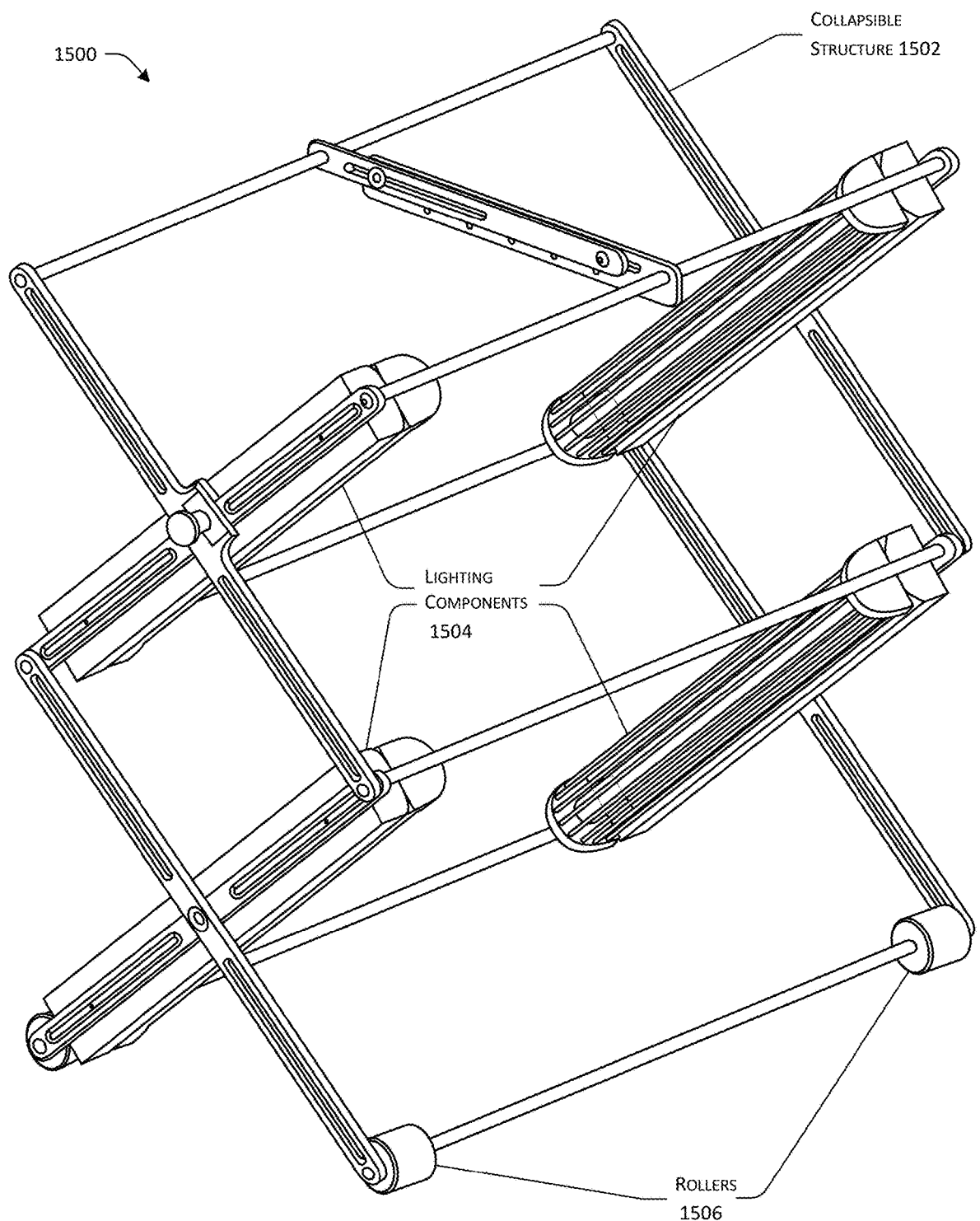
FIG. 15 is a pictorial diagram of an illustrative system that includes a structure and multiple lighting components that are used to sanitize or disinfect an object placed within the illustrative system depicted in FIG. 14, where the illustrative system is in an expanded state.

FIG. 15 is a pictorial diagram 1500 of a collapsible structure 1502 that includes one or more lighting components 1504 and one or more rollers 1506. Although the apparatus 1400 illustrated in FIG. 14 is not depicted in FIG. 15, the collapsible structure 1502 is located within the apparatus 1400 for the purpose of sanitizing objects that are placed within the apparatus 1400. The collapsible structure 1502 can be transitioned from an expanded state/configuration (depicted in FIG. 15) to a collapsed or unexpanded state/configuration. That is, when the apparatus 1400 is in the expanded state, the collapsible structure 1502 will also be in the expanded state. Then, when the apparatus 1400 is in the collapsed or unexpanded state/configuration, the collapsible structure 1502 will also be in the collapsed or unexpanded state/configuration. During the transition from the expanded state to the unexpanded/collapsed state for the apparatus 1400, and vice versa, the rollers 1506 of the collapsible structure 1502 may allow the collapsible structure 1502 to transition between the expanded state and the unexpanded/collapsed state. In various embodiments, the rollers may alternatively be wheels or a different mechanism that allows the collapsible structure 1502 to transition (e.g., slide, roll, etc.) between the expanded and the unexpanded/collapsed state.

The collapsible structure 1502 may include one or more lighting components 1504 (e.g., lamps or other lights) attached thereto that emit light (e.g., UV light, UVC light, etc.). When an object is placed within the interior cavity of the apparatus 1400 and the lid 1406 of the apparatus 1400 is closed, the lighting components 1504 emit light that sanitizes the object(s). Although four lighting components are illustrated in FIG. 15, any number of lighting components 1504 are contemplated herein. Moreover, the configuration and/or orientation of the lighting components on the collapsible structure 1502 may be adjusted or modified, and may be adjusted/modified based on a type, size, shape, etc. of the object(s) to be sanitized such that all surfaces of the object(s) are exposed to light emitted by the lighting components 1504.

Figure 16:
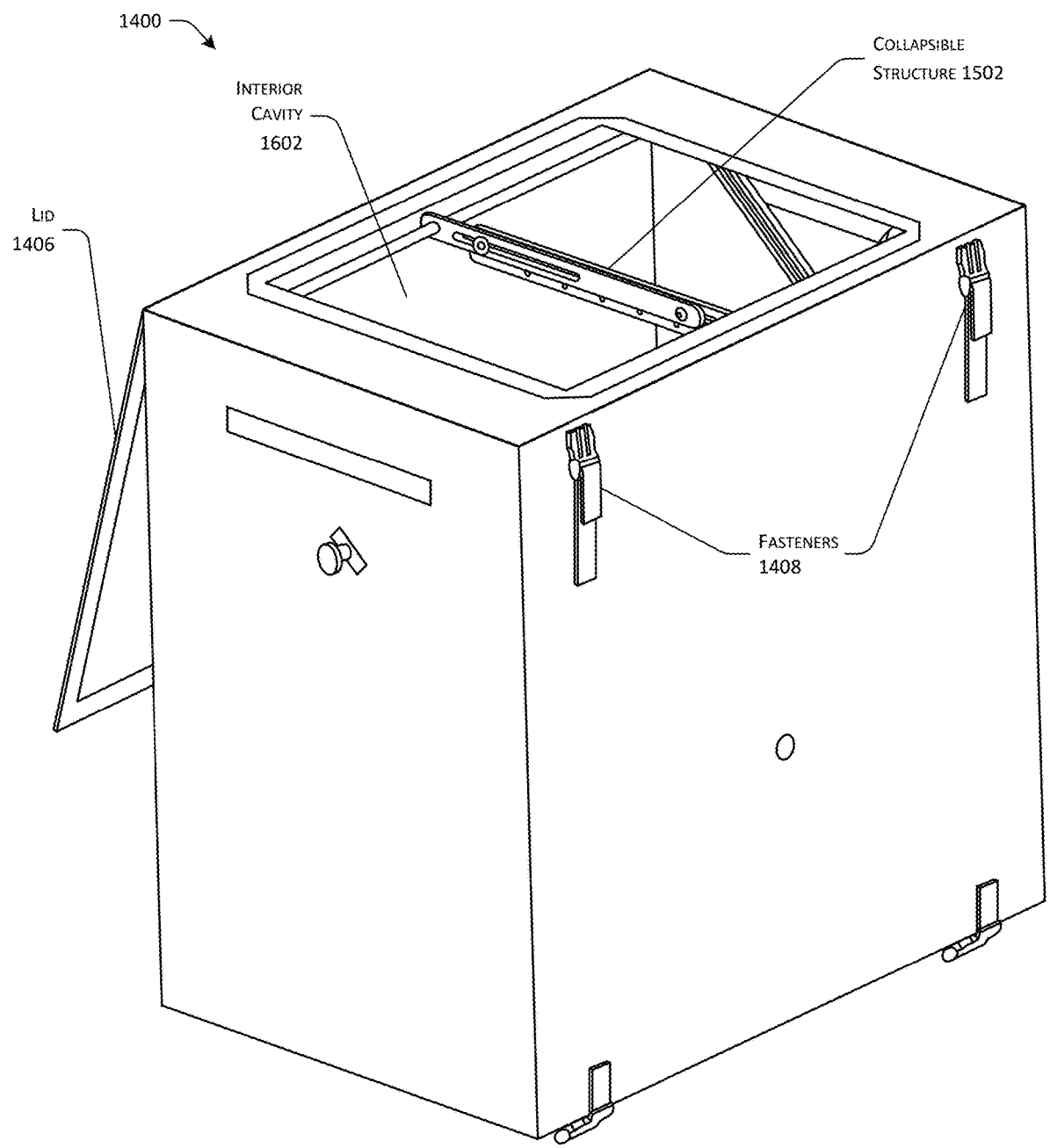
FIG. 16 is a pictorial diagram of the illustrative system depicted in FIG. 14, wherein a lid/cover of the illustrated system is in an open configuration.

FIG. 16 is a pictorial diagram of the apparatus 1400 illustrated in FIG. 14. Unlike FIG. 14, however, the apparatus 1400 depicted in FIG. 16 has the lid 1406 in the open position or configuration. A user/operator has undone the fasteners 1408 in order to open the lid 1406, thereby revealing, and providing access to, the interior cavity 1602 of the apparatus 1400. When the lid 1406 is in the open configuration/state, and when the apparatus 1400 is in the expanded state/configuration (as shown in FIG. 16), a user may place one or more objects to be sanitized within the interior cavity 1602. As shown, the collapsible structure 1502 that includes the one or more lighting components 1504 is within the interior cavity 1602 of the apparatus 1400. The object(s) may be placed on a bottom surface within the interior cavity 1602, or the object(s) may be placed upon, or hung from, the collapsible structure 1502 itself or from/on one or more structural components within the interior cavity 1602. Such structural components may include hangers, one or more bars/poles, racks, hooks/pins/nails, platforms, shelves, and any other mechanism in which object(s) may be hung from or place upon. After placing the object(s) within the interior cavity 1602, closing the lid 1406, and fastening the fasteners 1408, the object(s) may be sanitized within the apparatus 1400. For instance, a user may turn on the lighting components 1504 using a control mechanism, such as a user interface, a switch, a button, a control panel, a mobile application residing on a mobile device, etc. Such control mechanism may be located on the apparatus 1400, the collapsible structure 1502, and/or the lighting components 1504, the control mechanism may be connected to the apparatus 1400 via one or more wires, or the control mechanism may be connected wirelessly to the apparatus 1400 (e.g., WiFi, Bluetooth, etc.).

In some embodiments, the lighting components 1504 are powered on and powered off via a power cord having a male end and female end. Either the male end or the female end may protrude via the top portion of the apparatus 1400 and/or via a hole within an exterior surface of the apparatus 1400. The apparatus also has a main power cord that is plugged into any type of outlet, such as a wall outlet, a power strip, and so on. The main power cord enables the apparatus to be powered on/off as a result of the male end and the female end of the power cord being connected.

The following example illustrates how an object is to be sanitized by the apparatus 1400. Initially, the lighting components 1504 are enabled to be powered on/off by first plugging the main power cord into an outlet. Provided that the apparatus 1400 is in the expanded configuration, and once one or more objects are placed within the interior cavity 1602 of the apparatus 1400, the lid 1406 of the apparatus 1400 is closed and the fasteners 1408 are connected. Connecting the fasteners 1408 may help secure the lid 1406 in place. Then, in order to activate or power on the lighting components 1504, the male end and the female end of the power cord are connected. In some embodiments, the male end of the power cord is connected to the lid 1406, while the female end of the power cord is connected to the front lower center portion of the apparatus 1400, although the female end may be connected to any side surface of the apparatus 1400. Once the male end and the female end are connected to one another, the lighting components 1504 will be powered on and will emit light towards the object to be sanitized. In certain embodiments, the lid 1406 will need to be closed in order for the male end and the female end of the power cord to reach one another. To power off/disactivate the lighting components 1504, and provided that the object(s) within the interior cavity 1602 of the apparatus 1400 have been exposed to the light for the specified duration of time and have been disinfected/sanitized, the male and female end of the power cord are disconnected. This will power off the lighting components 1504 such that no more light will be emitted. The object(s) within the interior cavity 1602 of the apparatus may be retrieved by undoing the fasteners 1408, opening the lid 1406, and removing the object(s) from the interior cavity 1602.

Figure 17:
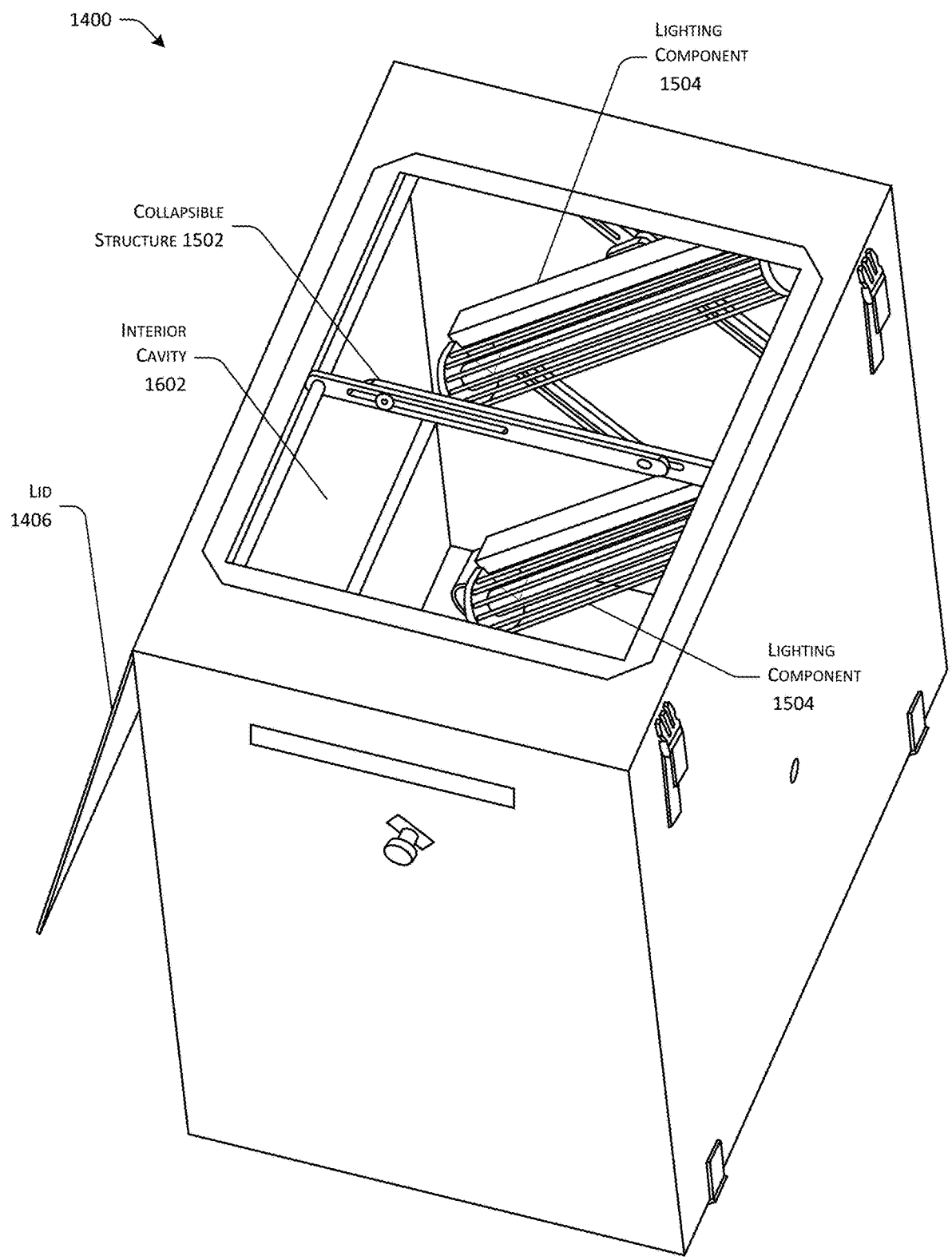
FIG. 17 is a pictorial diagram of the illustrative system depicted in FIG. 16, wherein the illustrative system is shown from a different viewpoint and depicts the illustrative system depicted in FIG. 15 within an interior cavity of the illustrative system.

FIG. 17 is a pictorial diagram of the apparatus 1400 illustrated in FIGS. 14 and 16. In FIG. 17, the apparatus 1400 is shown from a different perspective/angle as compared to FIG. 16. Here, FIG. 14 depicts an overhead view of the apparatus 1400 such that the interior cavity 1602 of the apparatus 1400 is visible. Within the interior cavity 1602 is the collapsible structure 1502, which includes the lighting components 1504. Similar to FIG. 16, the lid 1406 of the apparatus 1400 is in the open configuration/state, where an object to be sanitized may be placed within the interior cavity 1602 of the apparatus 1400.

Figure 18:
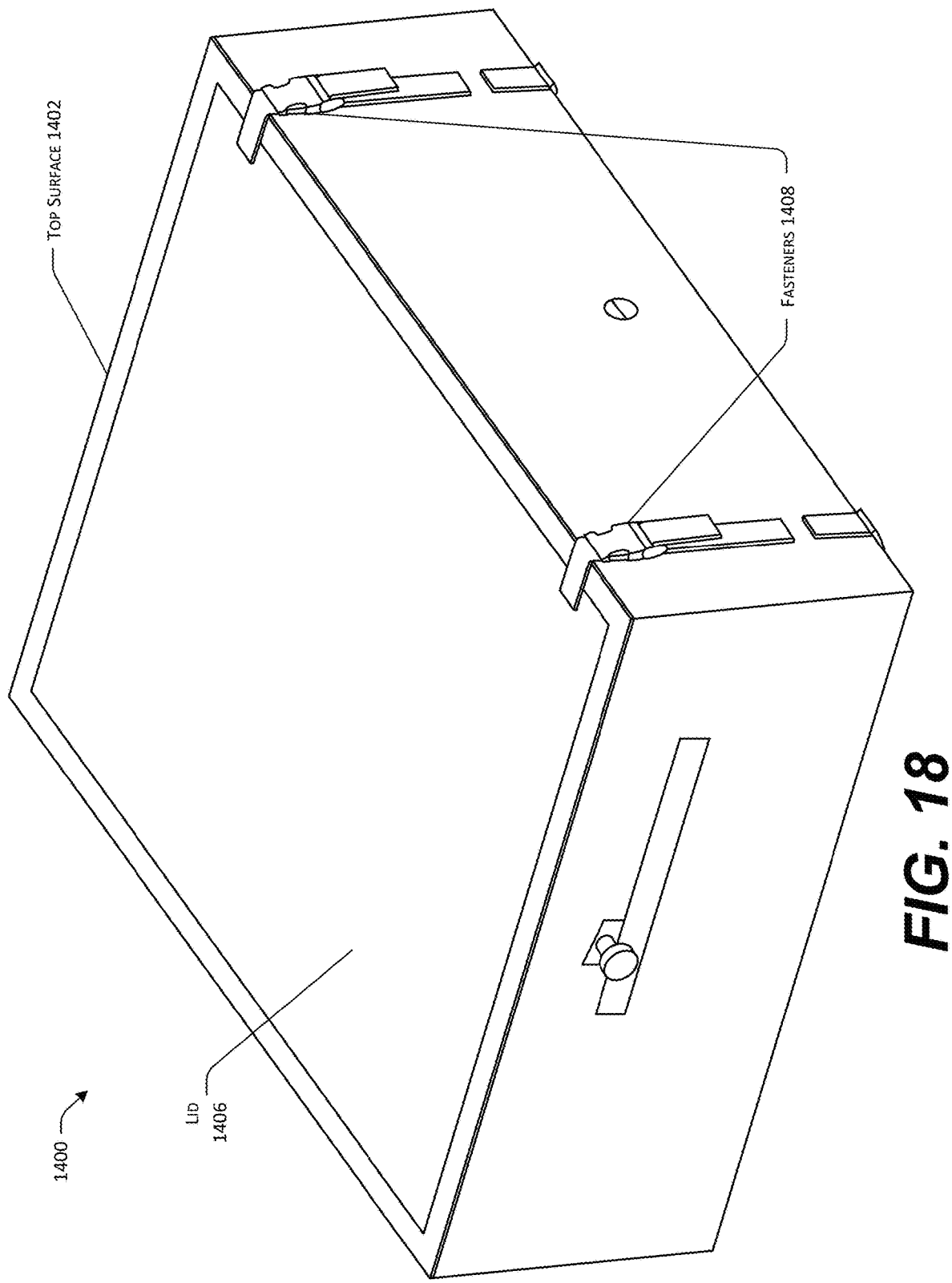
FIG. 18 is a pictorial diagram of the illustrative system depicted in FIG. 14, where the illustrative system is in a collapsed/unexpanded state and is in the closed configuration.

FIG. 18 is a pictorial diagram of the apparatus 1400 as depicted in FIG. 14. In this embodiment, the apparatus is in the unexpanded or collapsed state/configuration and, when in the unexpanded/collapsed state, the apparatus 1400 is unavailable to sanitize objects. However, to sanitize objects, the apparatus 1400 need only be transitioned from the unexpanded/collapsed state to the expanded state. As shown in FIG. 18, the lid 1406 of the apparatus 1400 is in the closed configuration and the fasteners 1408 are fastened to prevent the lid 1406 from opening. If the lid 1406 were to inadvertently open, the collapsible structure 1502 and/or the lighting components 1504 could potentially fall out of the apparatus 1400 or otherwise become damaged. When the apparatus 1400 is in the collapsed/unexpanded state, the apparatus 1400 may be more compact and easier to transport or store.

Figure 19:
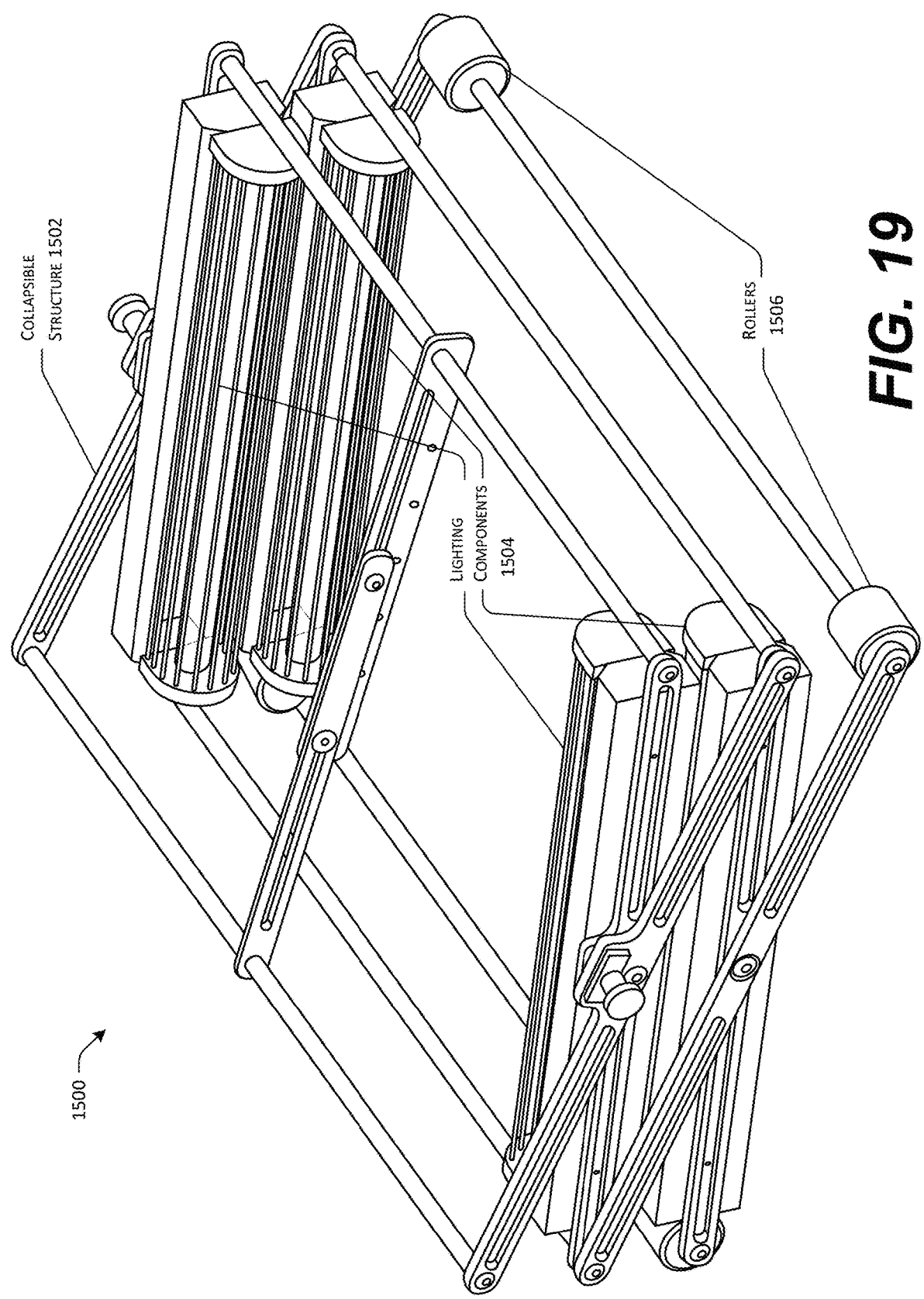
FIG. 19 is a pictorial diagram of the illustrative system depicted in FIG. 15, where the illustrative system is in a collapsed/unexpanded state.

FIG. 19 is a pictorial diagram of the collapsible structure 1502 in the collapsed/unexpanded state. For instance, the collapsible structure 1502 may be in the collapsed/unexpanded state when the apparatus 1400 is in the collapsed/unexpanded state, as depicted in FIG. 18. Similar to FIG. 15, the collapsible structure 1502 includes the lighting components 1504 and the rollers 1506, which allow the collapsible structure 1502 to transition from the expanded state to the collapsed/unexpanded state. When the collapsible structure 1502 is in the collapsed/unexpanded state, the lighting components 1504 on the same side of the collapsible structure 1502 become stacked with respect one another, causing the collapsible structure 1502 to become more compact.

Figure 20:
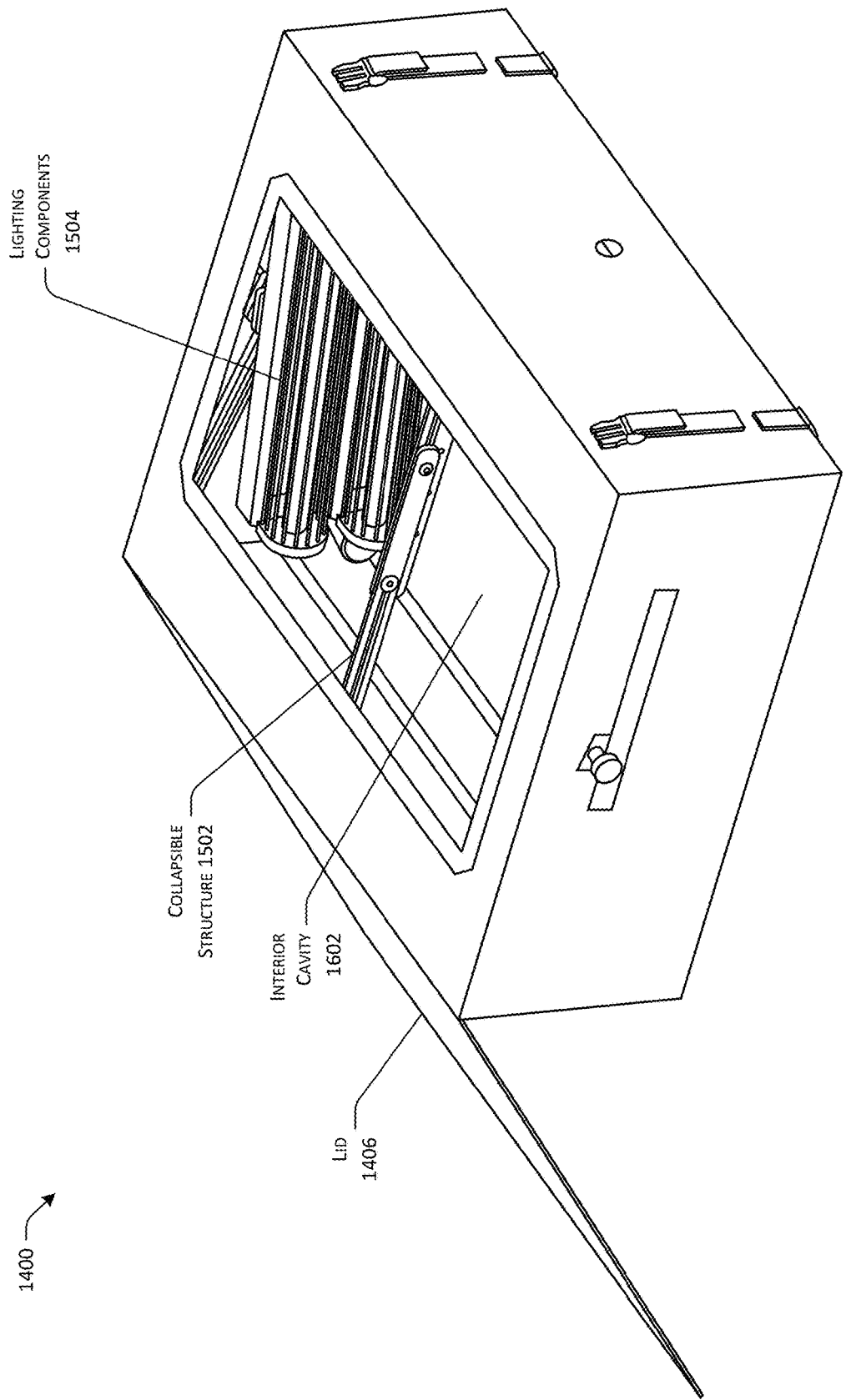
FIG. 20 is a pictorial diagram of an illustrative system depicted in FIG. 18, where the illustrative system is in the collapsed/unexpanded state and the lid/cover is in an open configuration.

FIG. 20 is a pictorial diagram of the apparatus 1400 as shown in FIG. 18, where the apparatus 1400 and the collapsible structure 1502 within the interior cavity 1602 of the apparatus 1400 are both in the unexpanded/collapsed state. In FIG. 20, the lid 1406 is open to depict the collapsible structure 1502, as well as the lighting components 1504, within the interior cavity 1602 of the apparatus 1400.

Figure 21:
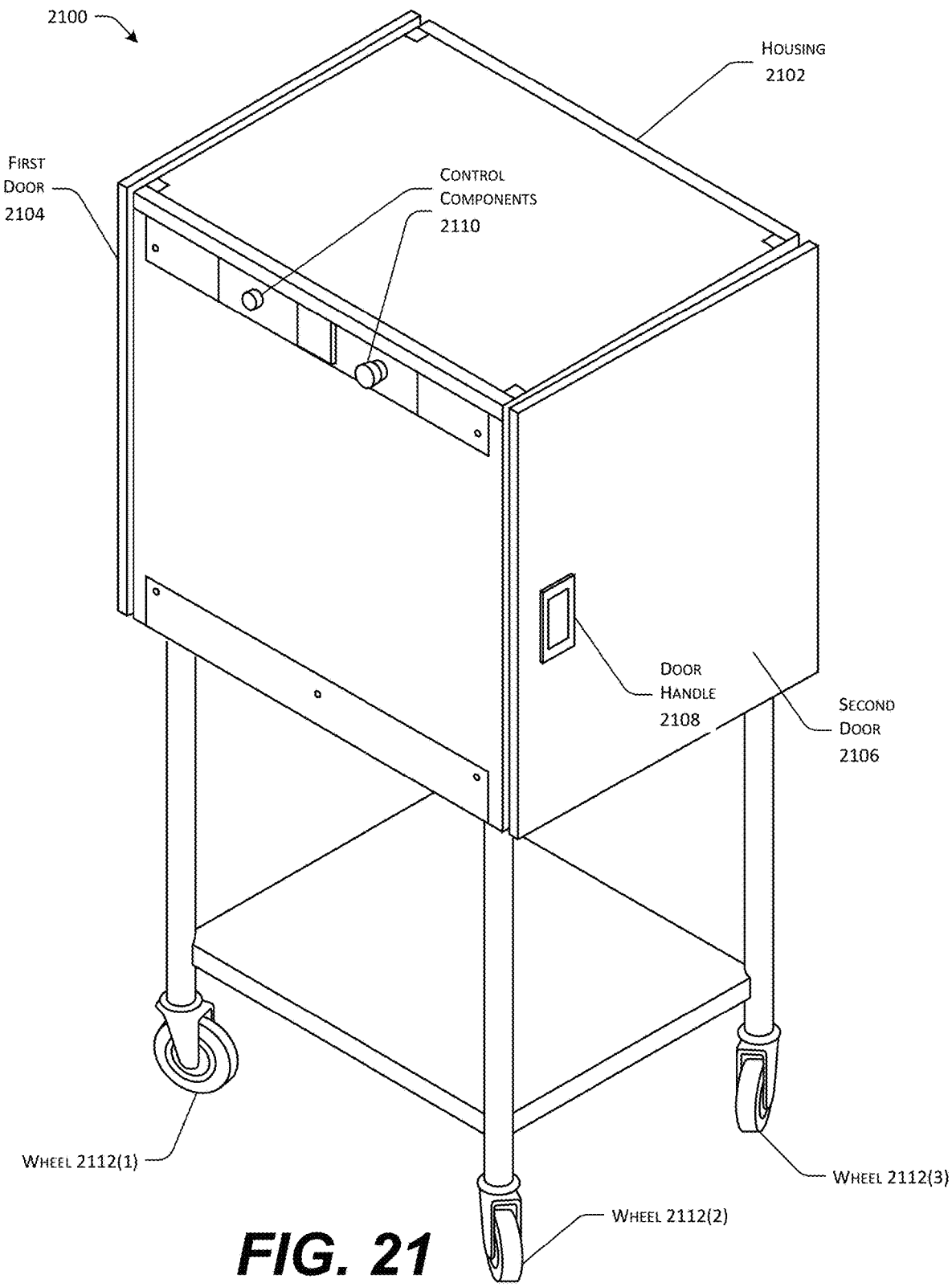
FIG. 21 is a pictorial diagram of an illustrative system that uses light to sanitize and/or disinfect an object, where the illustrative system includes two doors that open and close to insert and remove the object and where the two doors are in a closed configuration.

FIG. 21 is a pictorial diagram of an apparatus 2100 that is used to sanitize and disinfect objects. In particular, and although not shown in FIG. 21, the apparatus 2100 includes an interior cavity that includes one or more lighting components (e.g., UV lamps, UVC lamps, etc.) that emit light (e.g., UV light, UVC light, etc.) onto surfaces of objects to be sanitized. As will be discussed herein, the apparatus 2100 may be mobile in nature, thereby allowing the apparatus 2100 to be moved between different locations. As a result, the apparatus 2100 may be suitable for sanitizing smaller items, such as PPE (e.g., face masks, face shields, safety glasses, exam gloves, head coverings, etc.), handheld objects, personal electronic devices, and so on. Provided that the object to be sanitized by the apparatus 2100 is PPE within a medical facility, the PPE may be reused by doctors, nurses, other personnel, etc., instead of having to be discarded after a single use. Since the apparatus 2100 may destroy/eliminate all, or nearly all, of viruses, bacteria, and other pathogens that are potentially harmful to humans, doctors, nurses, patients, and other personnel would be afforded greater safety and protection as a result of use of the apparatus 2100.

In some embodiments, the apparatus 2100 may have a housing 2102 that encapsulates an interior cavity of the apparatus 2100. The housing 2102 may be made of any rigid material, including metal (e.g., stainless steel), plastic (or other polymer, synthetic, or semi-synthetic materials), wood, and so on. The apparatus 2100 may include one or more doors that provide access to the interior cavity, such as a first door 2104 and a second door 2106. As shown, the first door 2104 and the second door 2106 are disposed on opposite side surfaces of the apparatus 2100 such that the interior cavity of the apparatus 2100 can be accessed from multiple sides. Although two doors are shown here, a single door or more than two doors are contemplated herein, and the doors may be disposed on any side surface of the apparatus 2100, a front/back surface of the apparatus 2100, and/or on a top surface of the apparatus 2100. The doors appear to occupy an entirety of a side surface of the apparatus, but the doors may also take up only a portion of a surface of the apparatus 2100, such as being similar to a window. Although not necessary, each of the doors may include a door handle 2108 to facilitate opening and/or closing of the doors. For the purposes of FIGS. 21-24, the doors of the apparatus 2100 are in a closed configuration/state.

The apparatus may also include control components 2110, which allow an user/operator of the apparatus 2100 to turn on/off the lighting components, to specify a duration in which the lighting components are active (e.g., 30 seconds, one minute, five minutes, etc.), and/or specify a frequency or wavelength of light emitted by the lighting components. The control components 2110 may include a user interface, one or more switches, buttons, levers, etc., a control panel, a mobile application residing on a mobile device, etc. The control components 2110 may be located on the apparatus 2100 at any location, may be connected to the apparatus 2100 via one or more wires, or may be connected wirelessly to the apparatus 2100 (e.g., WiFi, Bluetooth, etc.). The apparatus 2100 may also have one or more wheels 2112(1)-

2112(3) (or another mechanism) that allows the apparatus 2100 to be moved between different locations.

Figure 22:
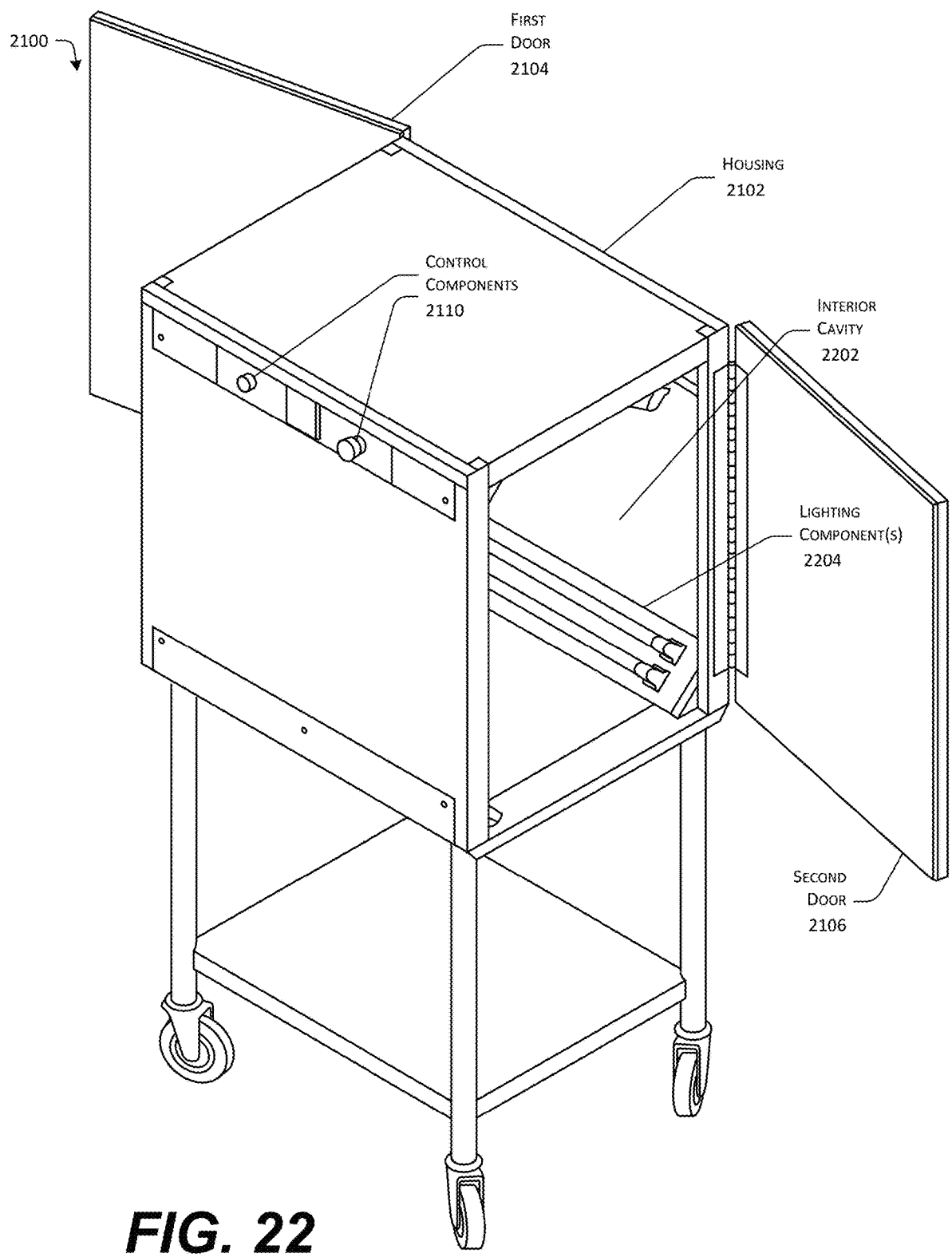
FIG. 22 is a pictorial diagram of the illustrative system depicted in FIG. 21, where the doors are in an open configuration.

FIG. 22 is a pictorial diagram of the apparatus 2100 as depicted in FIG. 21. However, in FIG. 22, the doors of the apparatus 2100 (i.e., the first door 2104 and the second door 2106) are in the open configuration/state such that the interior cavity 2202 of the apparatus 2100 is both visible and accessible. Within the interior cavity 2202 are the one or more lighting components 2204. The lighting components may be UV or UVC lamps that emit UV or UVC light. An object to be sanitized (e.g., PPE) may be placed within the interior cavity 2202 of the apparatus. The object may be placed on a bottom surface within the interior cavity 2202, or the object may be hung or placed upon some type of structure, such as one or more hooks/nails/pins, rods/bars, shelfs, platforms, racks, and so on. Regardless of how or where the object is placed within the interior cavity 2202, the lighting components 2204 emit light that is directed to the different surfaces of the object, thereby sanitizing/disinfecting the object. Upon placing one or more objects within the interior cavity 2202 and closing the doors, the lighting components 2204 may be activated (e.g., turned on) via the control components 2110 and the light emitted by the lighting components 2204 will sanitize the object(s). Once sanitized, the lighting components 2204 may be deactivated (e.g., turned off) and the object(s) may be removed from the apparatus 2100 via one or more of the first door 2104 and the second door 2106.

The light components 2204 may be of any number (e.g., one, two, three, four, etc.) and may be disposed at any location within the interior cavity 2202. For instance, and as depicted in FIG. 22, each lighting component 2204 may be disposed in a corner of the interior cavity 2202. For instance, two lighting components 2204 may be disposed in the interior cavity 2202 in corners that are adjacent to the inner bottom surface and the two inner side surfaces. Alternatively, or in addition, two lighting components 2204 may be disposed within the interior cavity 2202 in corners that are adjacent to the top inner surface and the two inner side surfaces. In that configuration, light may be emitted by the lighting components 2204 and toward the object(s) within the interior cavity 2202 from different directions. As described elsewhere herein, a position/location, angle, orientation, etc. of any one of the lighting components 2202 may be moved or shifted, possibly based on the type, shape, size, etc., of the object(s) to be sanitized.

Figure 23:
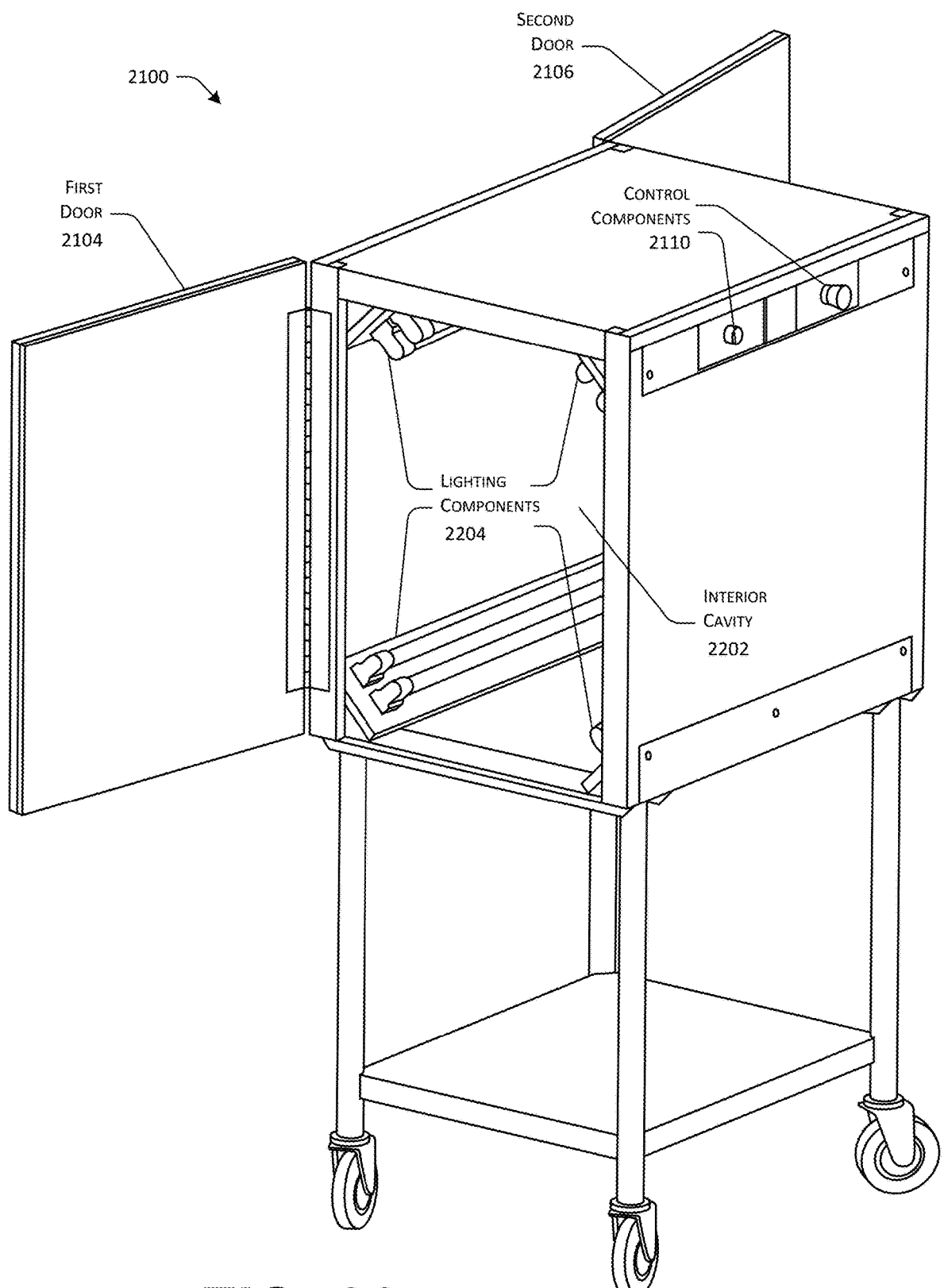
FIG. 23 is a pictorial diagram of the illustrative system depicted in FIG. 21, where the doors are in the open configuration and the illustrative system is shown from a different viewpoint as compared to FIG. 22.

FIG. 23 is a pictorial diagram of the apparatus 2100 depicted in FIGS. 21 and 22. Similar to FIG. 22, the doors of the apparatus 2100 are shown in the open configuration. In addition, FIG. 23 depicts each of the lighting components 2204 when the lighting components 2204 are disposed at each corner within the interior cavity 2202 of the apparatus 2100. Each of the lighting components 2204 is disposed at an angle (e.g., approximately 45 degrees) such that light is emitted towards a middle or center of the interior cavity 2202 where an object to be sanitized would be placed, hung, draped, etc. The lighting components 2204 may each have one or more bulbs, and two bulbs for each lighting component 2204 are depicted in FIG. 23. In some embodiments, lighting components 2204 may be disposed and affixed to the inner surface of the first door 2104 and/or the second door 2106. Moreover, lighting components 2204 may also be disposed on the inner side surfaces, the inner bottom surface, and/or the inner top surface of the interior cavity 2202 in order to expose objects to even more light/radiation.

Figure 24:
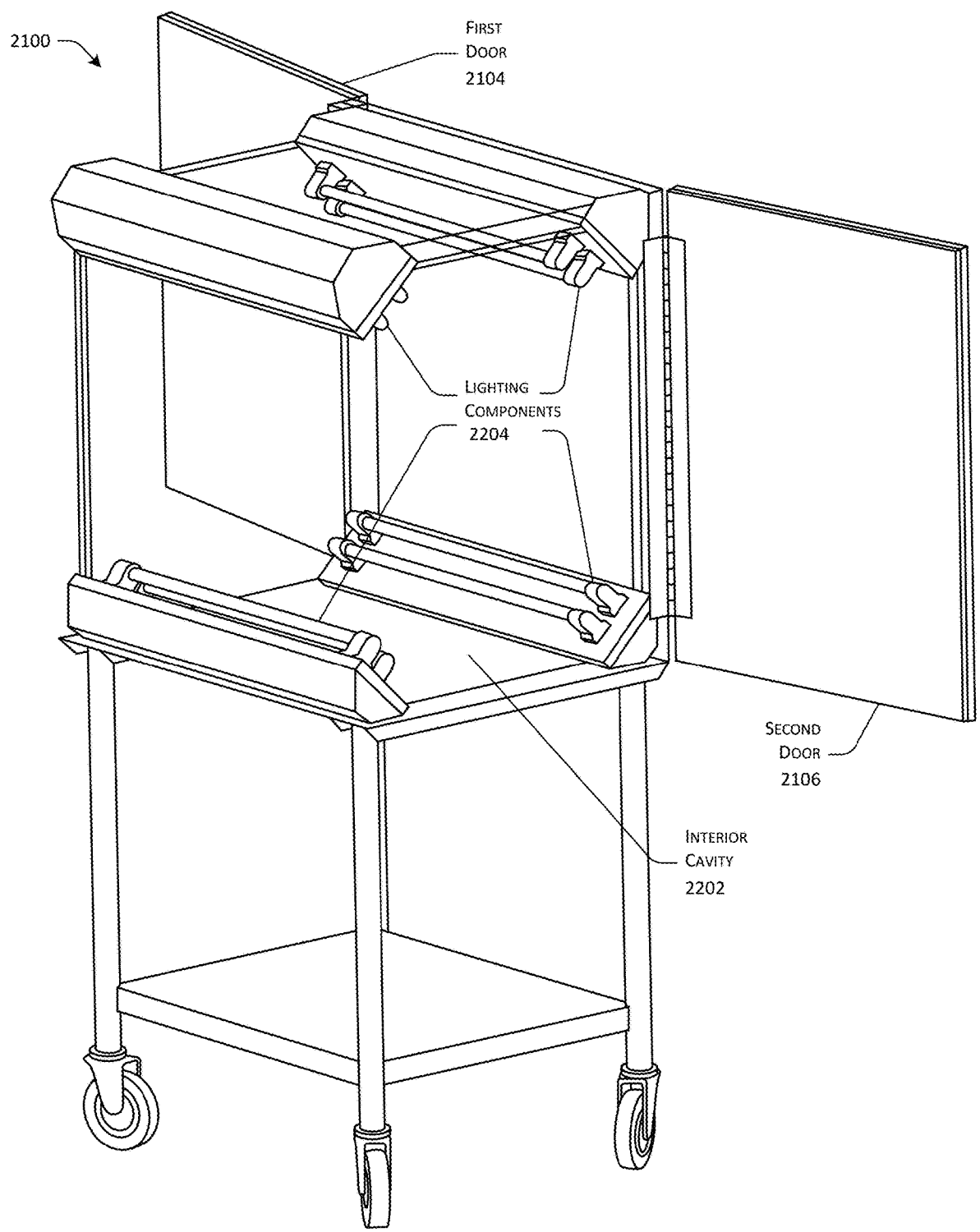
FIG. 24 is a pictorial diagram of the illustrative system depicted in FIG. 21, where the housing has been removed to show an interior cavity of the illustrative system.

FIG. 24 is a pictorial diagram of the apparatus 2100 depicted in FIGS. 21-23. In FIG. 24, the housing 2102 of the apparatus 2100 has been removed so that the interior cavity 2202 of the apparatus 2100 and the lighting component(s) 2204 within the interior cavity 2202 are more visible. The first door 2104 and the second door 2106 are again shown in the open configuration such that the interior cavity 2202 of the apparatus 2100 is visible and accessible. Similar to FIG. 23, the lighting components 2204 are disposed in each corner of the interior cavity 2202 and are angled towards the middle or center of the interior cavity 2202. Objects to be sanitized may be placed on the inner bottom surface of the interior cavity 2202, or they may be hung from, placed on, draped over, etc. any type of structural component, such as hooks, nails, platforms, shelves, racks, knobs, bars/poles, and so on.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A device configured to sanitize an object, comprising:
a housing including a lid that, when in an open configuration, provides access to an interior cavity of the device;
a collapsible structure disposed within the interior cavity; and
one or more lighting components that are affixed to the collapsible structure, wherein the one or more lighting components are configured to emit light directed towards the object at a time at which the object is within the interior cavity,
wherein the device and the collapsible structure are configured to transition between (1) an expanded state in which the one or more lighting components are configured to emit the light towards the object and (2) an unexpanded state in which the one or more lighting components are unable to emit the light towards the object.

2. The device as recited in claim 1, further comprising one or more fasteners that are disposed on an exterior surface of the housing, the one or more fasteners being configured to secure the lid to the housing when the lid is in a closed configuration.

3. The device as recited in claim 1, further comprising a power source that is configured to supply electric power to the one or more lighting components.

4. The device as recited in claim 1, further comprising a reflective surface disposed on each side surface and a bottom surface within the interior cavity.

5. The device as recited in claim 1, wherein the object is placed within the interior cavity via an opening that is accessible when the lid is in the open configuration.

6. The device as recited in claim 1, wherein the one or more lighting components include at least one first lighting component affixed to a first side of the collapsible structure and at least one second lighting component affixed to a second side of the collapsible structure that is opposite the first side.

7. The device as recited in claim 1, wherein the one or more lighting components include at least two first lighting components affixed to a first side of the collapsible structure and at least two second lighting components affixed to a second side of the collapsible structure that is opposite the first side, wherein, when the collapsible structure is in the unexpanded state, the at least two first lighting components are adjacent to one another and the at least two second lighting components are adjacent to one another.

8. The device as recited in claim 1, further comprising one or more handles disposed on one or more exterior surfaces of the housing, the one or more handles being used to transport the device.

9. A device configured to sanitize an object, comprising:
a housing that provides access to an interior cavity of the device;
a lid that, when in an open configuration, provides access to the interior cavity;
one or more fasteners that are disposed on an exterior surface of the housing, the one or more fasteners being configured to secure the lid to the housing when the lid is in a closed configuration;
a collapsible structure disposed within the interior cavity; and
one or more lighting components that are affixed to the collapsible structure, wherein the one or more lighting components emit light within the interior cavity at a time at which the object is within the interior cavity and when the device is in an expanded state,
wherein the device and the collapsible structure are configured to transition between (1) the expanded state in which the one or more lighting components are configured to emit within the interior cavity and (2) an unexpanded state in which the one or more lighting components refrain from emitting the light within the interior cavity.

10. The device as recited in claim 9, further comprising a power source that is configured to supply electric power to the one or more lighting components.

11. The device as recited in claim 9, further comprising a reflective surface disposed on each side surface and a bottom surface within the interior cavity.

12. The device as recited in claim 9, wherein the object is placed within the interior cavity via an opening that is accessible when the lid is in the open configuration.

13. The device as recited in claim 9, wherein the one or more lighting components include at least one first lighting component affixed to a first side of the collapsible structure and at least one second lighting component affixed to a second side of the collapsible structure that is opposite the first side.

14. The device as recited in claim 9, wherein the one or more lighting components include at least two first lighting components affixed to a first side of the collapsible structure and at least two second lighting components affixed to a second side of the collapsible structure that is opposite the first side, wherein, when the collapsible structure is in the unexpanded state, the at least two first lighting components are adjacent to one another and the at least two second lighting components are adjacent to one another.

15. The device as recited in claim 9, further comprising one or more handles disposed on at least one of the exterior surface or one or more other exterior surfaces of the housing, the one or more handles being used to transport the device.

16. The device as recited in claim 9, wherein the one or more lighting components are configured to emit the light when the lid is in the closed configuration and be disabled to emit emitting the light when the lid is in the open configuration.

17. A method comprising:
causing a lid of a device used to sanitize an object to open from a closed configuration to an open configuration, wherein the lid is part of a housing of the device and the lid, when in the open configuration, provides access to an interior cavity of the device; and
causing one or more lighting components that are affixed to a collapsible structure disposed within the interior cavity to emit light directed towards the object at a time at which the object is within the interior cavity, wherein the device and the collapsible structure are configured to transition between (1) an expanded state in which the one or more lighting components are configured to emit the light towards the object and (2) an unexpanded state in which the one or more lighting components are unable to emit the light towards the object.

18. The method as recited in claim 17, further comprising:
after the light is emitted towards the object for a predetermined duration of time, causing the object to be removed from the interior cavity via the lid;
causing the lid to close from the open configuration to the closed configuration;
causing one or more fasteners that are disposed on an exterior surface of the housing to secure the lid to the housing when the lid is in the closed configuration.

19. The method as recited in claim 17, wherein at least one of a side surface or a bottom surface within the interior cavity includes a reflective surface.

20. The method as recited in claim 17, wherein the one or more lighting components include at least one first lighting component affixed to a first side of the collapsible structure and at least one second lighting component affixed to a second side of the collapsible structure that is opposite the first side.

* * * * *